United States Patent
Welling et al.

(10) Patent No.: US 8,288,346 B2
(45) Date of Patent: Oct. 16, 2012

(54) COMPOSITION AND METHOD FOR THE TREATMENT OF HYPERKALEMIA

(75) Inventors: Paul A. Welling, Baltimore, MD (US); Liang Fang, Halethorpe, MD (US)

(73) Assignee: University of Maryland, Baltimore, Baltimore, MD (US)

(*) Notice: Subject to any disclaimer, the term of this patent is extended or adjusted under 35 U.S.C. 154(b) by 108 days.

(21) Appl. No.: 12/576,851

(22) Filed: Oct. 9, 2009

(65) Prior Publication Data

US 2010/0093634 A1 Apr. 15, 2010

Related U.S. Application Data

(60) Provisional application No. 61/104,247, filed on Oct. 9, 2008.

(51) Int. Cl.
*A61K 38/16* (2006.01)
*A61K 38/00* (2006.01)
*C07K 14/435* (2006.01)

(52) U.S. Cl. ........ 514/17.4; 514/1.1; 514/21.2; 530/350

(58) Field of Classification Search .................. None
See application file for complete search history.

(56) References Cited

OTHER PUBLICATIONS

Pettit et al. (1998). The development of site-specific drug-delivery systems for protein and peptide biopharmaceuticals. Trends in Biotechnology. 16: 343-349.*
Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Boim, M. et al., ROMK inwardly rectifying ATP-sensitive K+ channel II. Cloning and distribution of alternative forms, journal, 1995, Jan. 9, 1995, pp. F1132-F1140, the American Physiological Society, United States.
Bonifacino, J. et al., Signals for Sorting of Transmembrane Proteins to Endsomes and Lysosomes, journal, Mar. 6, 2003, pp. 395-447, United States.
Cassola, A. et al., Vasopressin increases density of apical low-conductance K+ channels in rat CCD, journal, 1993, pp. F502-F509, the American Physiological Society, United States.
Chen, W. et al., NPXY a Sequence Often Found in Cytoplasmic Tails, Is Required for Coated Pit-mediated Internalization of the Low Desity Lipoproptein Receptor, journal, Feb. 25, 1990, pp. 3116-3123, vol. 265, No. 6, The American Society for Biochemistry and Molecular Biology, Inc., United States.
Choe, H. et al., Structural Determinants of Gating in Inward-Rectifier K+ Channels, journal, Jan. 27, 1999, pp. 1988-2003, vol. 76, Biophysical Society, United States.
Chu, P. et al., Dietary potassium restriction stimulates endocytosis of ROMK channel in rat cortical collecting duct, journal, Aug. 27, 2003, pp. F1179-F1187, the American Physiological Society, United States.

Fang, L. et al., The ARH adaptor protein regulates endocytosis of the ROMK potassium secretary channel in the mouse kidney, journal, The Journal of Clinical Investigation, Nov. 2009, pp. 3278-3289, vol. 119, No. 11, United States.
Frindt, G. et al., Dissociation of K channel density and ROMK mRNA in rat cortical collecting tubule during K adaptation, journal, 1998, p. F524-F531, the American Physiological Society, United States.
Frindt, G. et al., Low-conductance K channels in apical membrane of rat cortical collecting tuble, journal, 1989, pp. F143-F151, the American Physiological Society, United States.
Garcia, C. et al., Autosomal Recessive Hypercholesterolemia Caused by Mutations in a Putative LDL Receptor Adaptor Protein, journal, Science, May 18, 2001, pp. 1394-1398, vol. 292, the American Association for Advancement of Science, United States.
Giebisch, G., Renal potassium transport: mechanisms and regulation, journal, AJP Centennial, 1998, pp. F817-F833, the American Physiological Society, United States.
He, G. et al., ARH Is a Modular Adaptor Protein That Interacts with the LDL Receptor, Clathrin, and AP-2, journal, The Journal of Biological Chemistry, Novemeber 15, 2002, pp. 44044-44049, vol. 277, No. 46, The American Society for Biochemistry and Molecular Biology, Inc., United States.
He, G. et al., Intersectin links WNK kinases to endocytosis of ROMK1, journal, The Journal of Clinical Investigation, pp. 1078-1087Apr. 2007, vol. 117, No. 4, United States.
Hebert S., Molecular Diversity and Regulation of Renal Potassium Channels, journal, Jan. 2005, pp. 319-371, vol. 85, the American Physiological Society, United States.
Ho, K. et al., Cloning and expression of an inwardly rectifying ATP-regulated potassium channel, journal, Mar. 4, 1993, pp. 31-38, vol. 362, Nature Publishing Group, United States.
Huang, D. et al, Impaired Regulation of Renal K+ Elimination in the sgk1-Knockout Mouse, journal, Journal of the American Society of Nephrology, Jan. 21, 2004, pp. 885-891, the American Society of Nephrology, United States.
Kahle, K. et al., WNK4 regulates theb alance between renal NaCl reabsorption and K+ secretion, journal, Nature Genetics, Nov. 9, 2003, pp. 372-377, vol. 45, No. 4, Nature Publishing Group, United States.

(Continued)

*Primary Examiner* — Christine J Saoud
*Assistant Examiner* — Jon M Lockard
(74) *Attorney, Agent, or Firm* — Evans & Molinelli PLLC; Judith A. Evans

(57) ABSTRACT

The internalization sequence at the C-terminal end of the ROMK protein has been identified and sequenced. It has been discovered determined that endocytosis is triggered by binding of the ROMK internalization sequence to ARH protein, which is co-localized and expressed with ROMK. New methods of treating or preventing hyperkalemia have been discovered that include administering to a patient who is at risk of developing hyperkalemia or who has hyperkalemia, a therapeutically effective amount of an agent that blocks the interaction of the ROMK internalization sequence with ARH protein, thereby preventing or reducing ARH-induced endocytosis of ROMK.

4 Claims, 8 Drawing Sheets

OTHER PUBLICATIONS

Keyel, P. et al., A Single Common Portal for Clathrin-mediated Endocytosis of Distinct Cargo Governed by Cargo-selective Adaptors, journal, Molecular Biology of the Cell, Jul. 19, 2006, pp. 4300-4317, vol. 17, The American Society for Cell Biology, United States.
Kohda, Y. et al., Localization of the ROMK potassium channel to the apical membrane of distal nephron in rat kidney, journal, Kidney International, May 12, 1998, pp. 1214-1223, vol. 54, the International Society of Nephrology, United States.
Kubo, Y. et al., International Union of Pharmacology. LIV. Nomenclature and Molecular Relationships of Inwardly Rectifying Potassium Channels, journal, Pharmacological Reviews, 2005, pp. 509-526, vol. 57, No. 4, The American Society for Pharmacology and Experimental Therapeutics, United States.
Kubokawa, M. et al., Role of Ca2+/CaMK II in Ca2+-induced K+ channel inhibition in rat CCD principal cell, journal, 1995, pp. F211-F219, the American Physiological Society, United States.
Lazrak, A. et al., Antagonistic regulation of ROMK by long and kidney-specific WNK1 isoforms, journal, Jan. 31, 2006, pp. 1615-1620, vol. 103, No. 5, The National Academy of Sciences of the USA, United States.
Leng, Q. et al., WNK3, a kinase related to genes mutated in hereditary hypertension with hyperkalemia, regulates the K+ channel RONK1 (Kir1.1), journal, Mar. 9, 2006, pp. 1-34, Physiology in Press, United States.
Lin, D. et al., K depletion increases proten tyrosine kinase-mediated phosphorylation of ROMK, journal, May 23, 2002, pp. F671-F677, the American Physiological Society, United States.
Lin, D. et al., Protein Kinase C (PKC)-induced Phosphorylation of ROMK1 Is Essential for the Surface Expressin of ROMK1 Channels, journal, The Journal of Biological Chemistry, Nov. 15, 2002, pp. 44278-44284, vol. 277, No. 46, The American Society for Biochemistry and Molecular Biology, Inc., United States.
Liu, Z. et al., Regulation of ROMK Channel and K+ Homeostasis by Kidney-specific WNK1 Kinase, journal, The Journal of Biological Chemistry, Jan. 22, 2009, pp. 12198-12206, vol. 284, No. 18, The American Society for Biochemistry and Molecular Biology, Inc., United States.
Lorenz, J. et al., Impaired Renal NaCl Absorptioin in Mice Lacking the ROMK Potassium Channel, a Model for Type II Bartter's Syndrome, journal, The Journal of Biological Chemistry, Jul. 16, 2002, pp. 37871-37880, vol. 277, No. 40, The American Society for Biochemistry and Molecular Biology, Inc., United States.
Lu, M. et al., Absense of Small Conductance K+ Channel (SK) Activity in Apical Membranes of Thick Ascending Limb and Cortical Collecting Duct in ROMK (Bartter's) Knockout Mice, journal, The Journal of Biological Chemistry, Oct. 4, 2002, pp. 37881-37887, vol. 277, No. 40, JBC Papers in Press, United States.
Ma, D. et al., ER transport signals and trafficking of potassium channels and receptors, journal, 2002, pp. 287-292, Elsevier Science Ltd., United States.
Maurer, M. et al., The adaptor protein Dab2 sorts LDL receptors into coated pits independently of AP-2 and ARH, journal, Journal of Cell Science, Aug. 15, 2006, pp. 4235-4246, vol. 119, No. 20, The Company of Biologists, United States.
Mennitt, P. et al., Localization of ROMK Channels in the Rat Kidney, journal, Journal of the American Society of Nephrology, Aug. 12, 1997, pp. 1823-1830, the American Society of Nephrology, United States.
Mishra, S. et al., Disabled-2 exhibits the properties of a cargo-selective endocytic clathrin adaptor, journal, The EMBO Journal, 2002, pp. 4915-4926, vol. 21, No. 18, European Molecular Biology Organization.
Mishra, S. et al., The autosomal recessive hypercholesterolemia (ARH) protein interfaces directly with the clathrin-coat machinery, journal, Dec. 10, 2002, pp. 16099-16104, vol. 99, No. 25.
Morris, S. et al., Dual roles for the Dab2 adaptor protein in embryonic development and kidney transport, journal, The EMBO Journal, 2002, pp. 1555-1564, vol. 21, No. 7, European Molecular Biology Organization.
Nagai, M. et al., The Adaptor Protein ARH Escorts Megalin to and through Endsomes, journal, Molecular Biology of the Cell, Aug. 18, 2003, pp. 4984-4996, vol. 14, The American Society for Cell Biology, United States.
Nichols, C. et al., Mg2+-dependent inward rectification of ROMK1 potassium channels expressed in Xenopush oocytes, journal, Journal of Physiology, Septemeber 30, 1993, pp. 399-409, United States.
O'Connell, A. et al., Phosphorylation-regulated endoplasmic reticulum retention signal in the renal outer-medullary K+ channel (ROMK), journal, Jul. 12, 2005, pp. 9954-9959, vol. 102, No. 28, The National Academy of Sciences, United States.
Palmer, L. et al., Aldosterone and potassium secretion by the cortical collecting duct, journal, Kidney International, 2000, pp. 1324-1328, vol. 57, International Society of Nephrology, United States.
Palmer, L. et al., Regulation of Apical K and Na Channels and Na/K Pumps in Rat Cortical Colelcting Tubule by Dietary K, journal, Oct. 1994, pp. 693-710, vol. 104, The Rockefeller University Press, United States.
Palmer, L. et al., Regulation of apical K channels in rat cortical collecting tubule during changes in dietary K intake, journal, 1999, pp. F805-F812m, the American Physiological Society, United States.
Palmer, L., Potassium secretion and the regulation of distal nephron K channels, journal, 1999, pp. F821-F825, the American Physiological Society, United States.
Ranganathan, S. et al., Serine and Threonine Phosphorylation of the Low Density Lipoprotein Receptor-related Protein Kinase C Regulates Endytosis and Association with Adapter Molecules, journal, The Journal of Biological Chemistry, Jul. 19, 2004, pp. 40536-40544, vol. 279, No. 39.
Ring, A. et al., An SGK1 site in WNK4 regulates Na+ channel and K+ channel activity and has implications for aldosterone signaling and K+ homeostasis, journal, Mar. 6, 2007, pp. 4025-4029, vol. 104, No. 10, The National Academy of Sciences of the USA, United States.
Santolini, E. et al., Numb Is an Endcytic Protein, journal, The Journal of Cell Biology, Dec. 11, 2000, pp. 1345-1351, vol. 151, No. 6, The Rockefeller University Press, United States.
Shuck, M. et al., Cloning and Characterization of Two K+ Inward Rectifier (Kir) 1.1 Potassium Channel Homologs from Human Kidney, journal, The Journal of Biological Chemistry, Jan. 3, 1997, pp. 586-593, vol. 272, No. 1, The American Society for Biochemistry and Molecular Biology, Inc., United States.
Sterling, H. et al., Inhibition of Protein-tyrosine Phosphatase Stimulates the Dynamin-dependent Endocytosis of ROMK1, journal, The Journal of Biological Chemistry, Feb. 8, 2002, pp. 4317-4323, vol. 277, No. 6, The American Society for Biochemistry and Molecular Biology, Inc., United States.
Stockklausner, C. et al., Surface Expression of Inward Rectifier Potassium Channels Is Controlled by Selective Golgi Export, journal, The Journal of Biological Chemistry, May 9, 2003, pp. 17000-17005, vol. 278, No. 19, The American Society for Biochemistry and Molecular Biology, Inc., United States.
Traub, L. et al., Decoding ubiquitin sorting signals for clathrin-dependent endocytosis by CLASPS, journal, Journal of Cell Science, Jan. 2, 2007, pp. 543-553, The Company of Biologists.
Uhlik, M. et al., Structural and Evolutionary Division of Phosphotyrosine Binding (PTB) Domains, journal, 2004, pp. 1-20, Elsevier Ltd.
Wade, J. et al., WNK1 kinase isoform switch regulates renal potassium excretion, journal, May 30, 2006, pp. 8558-8563, vol. 103, No. 22, United States.
Wang, W. et al., A potassium channel in the apical membrane of rabbit thick ascending limb of Henle's loop, journal, 1990, pp. F244-F253, the American Physiological Society, United States.
Wang, W. et al., Dual Effect of Adenosine Triphosphate on the Apical Small Conductance K+ Channel of the Rat Cortical Collecting Duct, journal, Jul. 1991, pp. 35-61, vol. 98, The Rockefeller University Press, United States.
Wang, W. et al., Two types of K+ channel in thick ascending limb of rat kidney, journal, 1994, pp. F599-F605, the American Physiological Society, United States.
Wei, Y. et al., Effect of dietary K intake on apical small-conductance K channel in CCD: role of protein tyrosine kinase, journal, Apr. 6, 2001, pp. F206-F212, the American Physiological Society, United States.
Wei, Y. et al., Protein-tyrosine Phosphatase Reduces the Number of Apical Small Conductance $K^+$ Channels in the Rat Cortical Collecting Duct, journal, The Journal of Biological Chemistry, Jul. 7, 2000, pp. 20502-20507, vol. 275, No. 27, The American Society for Biochemistry and Molecular Biology, Inc., United States.

Welling, P. et al., A comprehensive guide to the ROMK potassium channel: form and function in health and disease, journal, May 15, 2009, pp. F849-F863, the American Physiological Society, United States.

Wenhui, W. et al., Regulation of small-conductance K+ channel in apical membrane of rat cortical tubule, journal, 1990, pp. F494-F502, the American Physiological Society, United States.

Wilson, F. et al., Human Hypertension Caused by Mutations in WNK Kinases, journal, Aug. 10, 2001, pp. 1107-1112, vol. 293, United States.

Xu, J. et al., Localization of the ROMK protein on apical membranes of rat kidney nephron segments, journal, 1997, pp. F739-F748, the American Physiological Society, United States.

Yoo, D. et al., A Phosphorylation-dependent Export Structure in ROMK (Kir 1.1) Channel Overrides and Endoplasmic Reticulum Localization Signal, journal, The Journal of Biological Chemistry, Oct. 21, 2005, pp. 35281-35289, vol. 280, No. 42, The American Society for Biochemistry and Molecular Biology, Inc., United States.

Yoo, D. et al., Cell Surface Expression of the ROMK (Kir 1.1) Channel Is Regulated by the Aldosterone-induced Kinase, SGK-1, and Protein Kinase A, journal, The Journal of Biological Chemistry, Jun. 20, 2003, pp. 23066-23075, vol. 278, No. 25.

Zeng, W. et al., Evidence for endocytosis of ROMK potassium channel via clathrin-coated vesicles, journal, Apr. 9, 2002, pp. F630-F639, the American Physiological Society, United States.

Zhou, H. et al., Primary structure and functional properties of an epithelial K channel, journal, 1994, pp. C809-C824, the American Physiological Society, United States.

* cited by examiner

FIG. 6
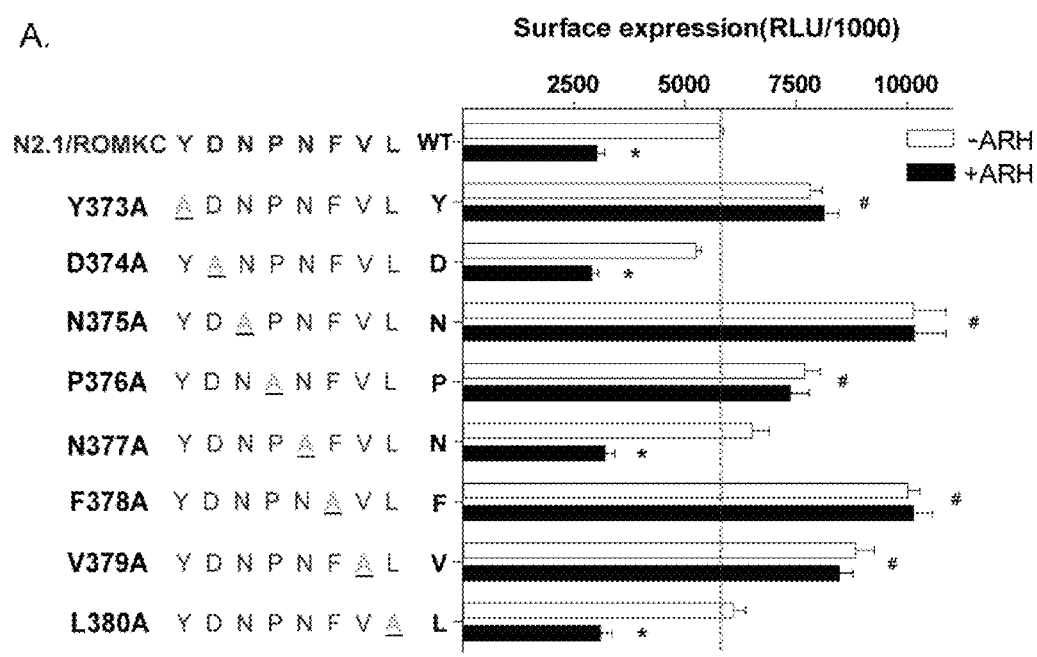

FIG. 7   ARH-Signal Recognition Site
Determinants of Binding are Identical to Determinants of Endocytosis
ARH-ROMK Binding Assay
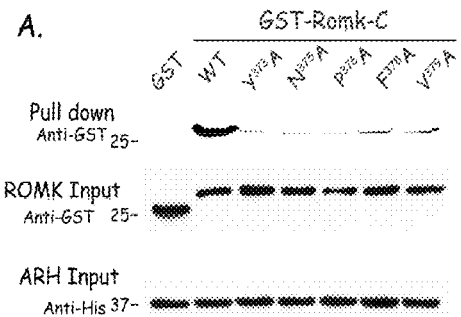
Internalization Rate
(ROMK + ARH)
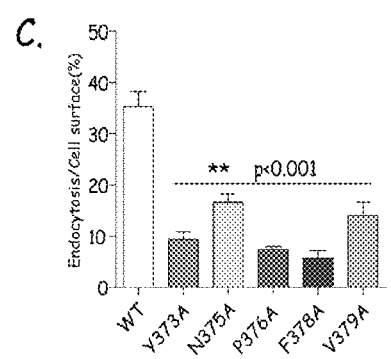
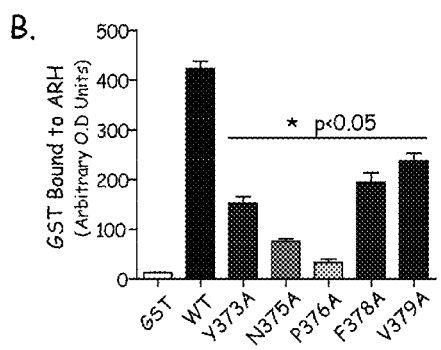

FIG. 8
A.
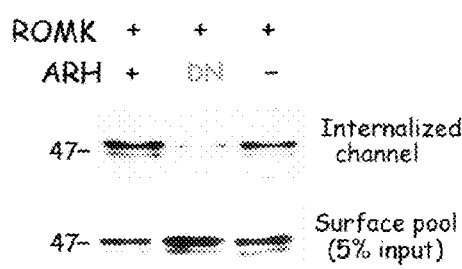
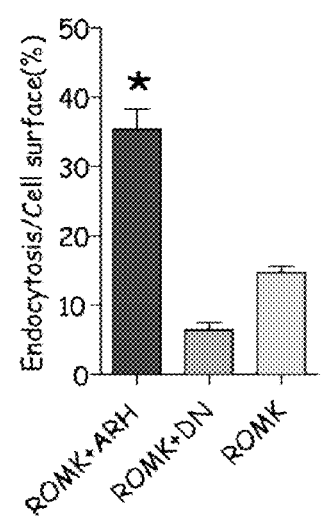
B.
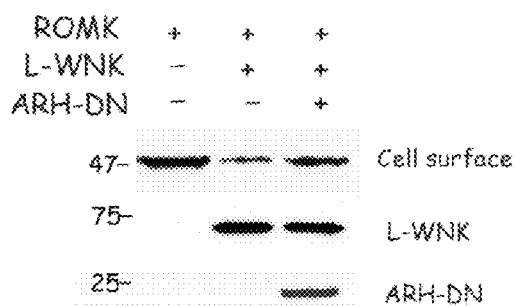
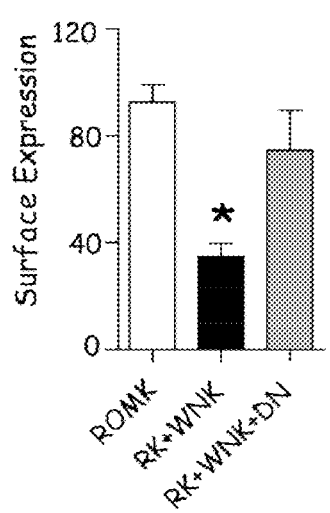

SEQUENCE LISTING

<160> NUMBER OF SEQ ID NOS: 10

<210> SEQ ID NO 1
<211> LENGTH: 2332
<212> TYPE: DNA
<213> ORGANISM: Homo sapiens

<400> SEQUENCE: 1

```
gtctgcatag aaagaccaac aaccagcacc acttccttgc ttttccagc catgaatgct      60 tccagtcgga atgtgtttga cacgttgatc agggtgttga cagaaagtat gttcaaacat     120
cttcggaaat gggtcgtcac tcgctttttt gggcattctc ggcaaagagc aaggctagtc     180
tccaaagatg gaaggtgcaa catagaattt ggcaatgtgg aggcacagtc aaggtttata     240
ttctttgtgg acatctggac aacggtactt gacctcaagt ggagatacaa aatgaccatt     300
ttcatcacag ccttcttggg gagttggttt ttctttggtc tcctgtggta tgcagtagcg     360
tacattcaca aagacctccc ggaattccat ccttctgcca atcacactcc ctgtgtggag     420
aatattaatg gcttgacctc agcttttctg ttttctctgg agactcaagt gaccattgga     480
tatggattca ggtgtgtgac agaacagtgt gccactgcca tttttctgct tatctttcag     540
tctatacttg gagttataat caattctttc atgtgtgggg ccatcttagc caagatctcc      600
```

-continued

```
aggcccaaaa aacgtgccaa gaccattacg ttcagcaaga acgcagtgat cagcaaacgg    660
ggagggaagc tttgcctcct aatccgagtg gctaatctca ggaagagcct tcttattggc    720
agtcacattt atggaaagct tctgaagacc acagtcactc ctgaaggaga gaccattatt    780
ttggaccaga tcaatatcaa ctttgtagtt gacgctggga tgaaaattt attcttcatc     840
tccccattga caatttacca tgtcattgat cacaacagcc ctttcttcca catggcagcg    900
gagacccttc tccagcagga ctttgaatta gtggtgtttt tagatggcac agtggagtcc    960
accagtgcta cctgccaagt ccggacatcc tatgtcccag aggaggtgct tggggctac   1020
cgttttgctc ccatagtatc caagacaaag aagggaaat accgagtgga tttccataac   1080
tttagcaaga cagtggaagt ggagacccct cactgtgcca tgtgccttta atgagaaa    1140
gatgttagag ccaggatgaa gagaggctat gacaacccca acttcatctt gtcagaagtc   1200
aatgaaacag atgacaccaa aatgtaacag tggcttttca acgggagtaa agcaaagtct   1260
ctaaagctcc tagtacctag aagcattatg aagcagtcaa caatttaggg gtacgaaagt   1320
aggatgagag ccttcaaagt ctaccagcac aaagacccct gagccccgca attgtgatcc   1380
cacaagacat gcatctccac aaggctactg tattagaacg tgcaatgcat ttatatgaaa   1440
ctggtgtatg aagacatag gtgctctctt gaaatcttaa atatgattat ttgagctcat   1500
ataaggtgga ttggagcaga taaaattatc aaaagtttca tgaacaggcc aaacaaaata   1560
tttttttaaag tttccttaaa gaagttatga actttagaaa ggatcagggg acaataataa   1620
tctcatttg attctactga taagaatgac tccactttta atgtggactt ttactcatgg   1680
aaaaattgtc tcctaatttg gggagatgaa ccaaccaatc aatgacaaga aaacgcttac   1740
acaaagaaca atttgaggct ctaagcttct catgtggtac gtttagacag aggctaaatc   1800
tgcacactag aatcttgatg ataccttcct gcaagacaga atgctttagt taaaagtggt   1860
gatgatattt ctttcaatct gtattggatg gcttaaaggg ctataaatct gtttataaag   1920
agcatttcct gctcttcgaa gacagcaatg aggagttgga aggtgcaaag tcagtagaga   1980
agggaatgta tcattaatgc acctgagaag aaacagtttc atgtgttcct ccacctagag   2040
tttgtactgg aatgctattt ctaaagaaga agtgggaaag agagaggaat gggatggagc   2100
cccacagtca gaatgttact atgtctttct ttccctgaca gcccatcttc ctaaaaggga   2160
ccagcttatg gaaggctcga ccttgagggg aaagttttac tgtgaaagtc ttcttcagat   2220
ccccacctgc atcattccga atgtgtcctg gaaaaaaact ggtactcaaa gctgcttagg   2280
aatcaaaatg tttcagtgt gttgattaat atagtaaatt tctgaaactg tg            2332
```

<210> SEQ ID NO 2
<211> LENGTH: 391
<212> TYPE: PRT
<213> ORGANISM: Homo sapiens

<400> SEQUENCE: 2

```
Met Asn Ala Ser Ser Arg Asn Val Phe Asp Thr Leu Ile Arg Val Leu
1               5                   10                  15

Thr Glu Ser Met Phe Lys His Leu Arg Lys Trp Val Val Thr Arg Phe
            20                  25                  30

Phe Gly His Ser Arg Gln Arg Ala Arg Leu Val Ser Lys Asp Gly Arg
        35                  40                  45

Cys Asn Ile Glu Phe Gly Asn Val Glu Ala Gln Ser Arg Phe Ile Phe
    50                  55                  60

Phe Val Asp Ile Trp Thr Thr Val Leu Asp Leu Lys Trp Arg Tyr Lys
65                  70                  75                  80
```

```
Met Thr Ile Phe Ile Thr Ala Phe Leu Gly Ser Trp Phe Phe Gly
                85                  90                  95
Leu Leu Trp Tyr Ala Val Ala Tyr Ile His Lys Asp Leu Pro Glu Phe
            100                 105                 110
His Pro Ser Ala Asn His Thr Pro Cys Val Glu Asn Ile Asn Gly Leu
        115                 120                 125
Thr Ser Ala Phe Leu Phe Ser Leu Glu Thr Gln Val Thr Ile Gly Tyr
    130                 135                 140
Gly Phe Arg Cys Val Thr Glu Gln Cys Ala Thr Ala Ile Phe Leu Leu
145                 150                 155                 160
Ile Phe Gln Ser Ile Leu Gly Val Ile Ile Asn Ser Phe Met Cys Gly
                165                 170                 175
Ala Ile Leu Ala Lys Ile Ser Arg Pro Lys Lys Arg Ala Lys Thr Ile
            180                 185                 190
Thr Phe Ser Lys Asn Ala Val Ile Ser Lys Arg Gly Gly Lys Leu Cys
        195                 200                 205
Leu Leu Ile Arg Val Ala Asn Leu Arg Lys Ser Leu Leu Ile Gly Ser
    210                 215                 220
His Ile Tyr Gly Lys Leu Leu Lys Thr Thr Val Thr Pro Glu Gly Glu
225                 230                 235                 240
Thr Ile Ile Leu Asp Gln Ile Asn Ile Asn Phe Val Val Asp Ala Gly
                245                 250                 255
Asn Glu Asn Leu Phe Phe Ile Ser Pro Leu Thr Ile Tyr His Val Ile
            260                 265                 270
Asp His Asn Ser Pro Phe Phe His Met Ala Ala Glu Thr Leu Leu Gln
        275                 280                 285
Gln Asp Phe Glu Leu Val Val Phe Leu Asp Gly Thr Val Glu Ser Thr
    290                 295                 300
Ser Ala Thr Cys Gln Val Arg Thr Ser Tyr Val Pro Glu Glu Val Leu
305                 310                 315                 320
Trp Gly Tyr Arg Phe Ala Pro Ile Val Ser Lys Thr Lys Glu Gly Lys
                325                 330                 335
Tyr Arg Val Asp Phe His Asn Phe Ser Lys Thr Val Glu Val Glu Thr
            340                 345                 350
Pro His Cys Ala Met Cys Leu Tyr Asn Glu Lys Asp Val Arg Ala Arg
        355                 360                 365
Met Lys Arg Gly Tyr Asp Asn Pro Asn Phe Ile Leu Ser Glu Val Asn
    370                 375                 380
Glu Thr Asp Asp Thr Lys Met
385                 390

<210> SEQ ID NO 3
<211> LENGTH: 2069
<212> TYPE: DNA
<213> ORGANISM: Rattus norvegicus

<400> SEQUENCE: 3
caatcacaca actccactcg agttagccat tgaaagccaa tgcaagtaaa tgtcattcca      60
aagcttaaga ttcattaagg tgggcctaaa agaagacagc tgctgtgcag acaacgtcga     120
acaagcacca cttgcttgct ttgcccagca tgggcgcttc ggaacggagt gtgttcagag     180
tgctgatcag ggcactgaca gaaaggatgt tcaaacacct ccgaagatgg tttatcactc     240
acatatttgg gcgttcccgg caacgggcaa ggctggtctc taaagaagga agatgtaaca     300
tcgagtttgg caatgtggat gcacagtcaa ggtttatatt ctttgtggac atctggacaa     360
```

```
ctgtgctgga cctgaaatgg aggtacaaaa tgaccgtgtt catcacagcc ttcttgggga    420
gttggttcct ctttggtctc ctgtggtatg tcgtagcgta tgttcataag gacctcccag    480
agttctaccc gcctgacaac cgcactcctt gtgtggagaa cattaatggc atgacttcag    540
cctttctgtt ttctctagag actcaagtga ccataggtta cggattcagg tttgtgacag    600
aacagtgcgc cactgccatt ttcctgctta tcttccagtc tattcttgga gtgatcatca    660
attccttcat gtgtggtgcc attttagcca agatctctag acccaaaaaa cgtgctaaaa    720
ccattacgtt cagcaagaat gcggtgatca gcaagcgtgg cgggaagctc tgcctcctca    780
tccgagtggc caatcttagg aagagccttc tgattggcag ccacatatat ggcaagcttc    840
taaagacaac catcactcct gaaggcgaga ccatcatttt ggatcagacc aacatcaact    900
tgtcgtcga cgctggcaat gaaaatttgt tcttcatatc cccactgacg atctaccaca    960
ttattgacca caacagccct ttcttccaca tggcagcaga aactctttcc aacaggact  1020
ttgagctggt ggtctttta gatggcacag tggaatccac cagtgcaacc tgccaggtcc    1080
gcacgtcata cgtcccagag gaggtgcttt ggggctaccg tttcgttcct attgtgtcca    1140
agaccaagga agggaaatac cgagttgatt ttcataactt cggtaagaca gtggaagtgg    1200
agacccctca ctgtgccatg tgcctctata tgagaaaga tgccagggcc aggatgaaga    1260
gaggctatga caaccctaac tttgtcttgt cagaagttga tgaaacggac dacacccaga    1320
tgtagcagtg gcttttccac ctacaaaaag cctcccaagg acctaagggt tgactgtgtt    1380
cagaagcatc tgacggggt ctgaaagcag atgagaaca tgcgaaatct gctagcacag    1440
tcaccctga accccagggc tatggttcta caagacacat agctctataa ggctgcatac    1500
ggtgcatgca tgtgaatgaa actgtggaag ccaaaggggc ccacttggat cctcactatg    1560
actgtgtaag ctcatatcgt gttgatggaa acaaagtcat tcaaggacaa aacttaggag    1620
ctttagaaag cttcaggaac tagccacatt tcctgtttga ttctatggat gagaaagatg    1680
ccatttttat cttaaagtag acttctatca atggaaaatc tgccctctgc gctgggaagt    1740
gagccagcca atcagtgaca ataagagact gtcatacaaa gaatcagtaa agactctaac    1800
cttctcaagc tctggtgttt gaagcctttg tctgagtctg gtccatgct tcagaagggg    1860
taaggtgaca tccactgact gtacctctct gaacccaagg tacagaagaa caggaagccc    1920
caatcaactt cataatcaac ccagatgctg cagcccatac agaatttggc ctgaatgatt    1980
tcctgtggag cattaaatgg aggccaagtc cactctttag atattaaatg aatattcttt    2040
tgcaaaggaa aaaaaaaaa aaaaaaaaa                                       2069
```

<210> SEQ ID NO 4
<211> LENGTH: 391
<212> TYPE: PRT
<213> ORGANISM: Rattus norvegicus

<400> SEQUENCE: 4

```
Met Gly Ala Ser Glu Arg Ser Val Phe Arg Val Leu Ile Arg Ala Leu
1               5                   10                  15

Thr Glu Arg Met Phe Lys His Leu Arg Arg Trp Phe Ile Thr His Ile
            20                  25                  30

Phe Gly Arg Ser Arg Gln Arg Ala Arg Leu Val Ser Lys Glu Gly Arg
        35                  40                  45

Cys Asn Ile Glu Phe Gly Asn Val Asp Ala Gln Ser Arg Phe Ile Phe
    50                  55                  60

Phe Val Asp Ile Trp Thr Thr Val Leu Asp Leu Lys Trp Arg Tyr Lys
```

```
                65                  70                  75                  80
Met Thr Val Phe Ile Thr Ala Phe Leu Gly Ser Trp Phe Leu Phe Gly
                    85                  90                  95

Leu Leu Trp Tyr Val Ala Tyr Val His Lys Asp Leu Pro Glu Phe
                100                 105                 110

Tyr Pro Pro Asp Asn Arg Thr Pro Cys Val Glu Asn Ile Asn Gly Met
                115                 120                 125

Thr Ser Ala Phe Leu Phe Ser Leu Glu Thr Gln Val Thr Ile Gly Tyr
        130                 135                 140

Gly Phe Arg Phe Val Thr Glu Gln Cys Ala Thr Ala Ile Phe Leu Leu
145                 150                 155                 160

Ile Phe Gln Ser Ile Leu Gly Val Ile Ile Asn Ser Phe Met Cys Gly
                165                 170                 175

Ala Ile Leu Ala Lys Ile Ser Arg Pro Lys Lys Arg Ala Lys Thr Ile
                180                 185                 190

Thr Phe Ser Lys Asn Ala Val Ile Ser Lys Arg Gly Gly Lys Leu Cys
                195                 200                 205

Leu Leu Ile Arg Val Ala Asn Leu Arg Lys Ser Leu Leu Ile Gly Ser
        210                 215                 220

His Ile Tyr Gly Lys Leu Leu Lys Thr Thr Ile Thr Pro Glu Gly Glu
225                 230                 235                 240

Thr Ile Ile Leu Asp Gln Thr Asn Ile Asn Phe Val Val Asp Ala Gly
                245                 250                 255

Asn Glu Asn Leu Phe Phe Ile Ser Pro Leu Thr Ile Tyr His Ile Ile
                260                 265                 270

Asp His Asn Ser Pro Phe Phe His Met Ala Ala Glu Thr Leu Ser Gln
        275                 280                 285

Gln Asp Phe Glu Leu Val Val Phe Leu Asp Gly Thr Val Glu Ser Thr
    290                 295                 300

Ser Ala Thr Cys Gln Val Arg Thr Ser Tyr Val Pro Glu Glu Val Leu
305                 310                 315                 320

Trp Gly Tyr Arg Phe Val Pro Ile Val Ser Lys Thr Lys Glu Gly Lys
                325                 330                 335

Tyr Arg Val Asp Phe His Asn Phe Gly Lys Thr Val Glu Val Glu Thr
                340                 345                 350

Pro His Cys Ala Met Cys Leu Tyr Asn Glu Lys Asp Ala Arg Ala Arg
                355                 360                 365

Met Lys Arg Gly Tyr Asp Asn Pro Asn Phe Val Leu Ser Glu Val Asp
        370                 375                 380

Glu Thr Asp Asp Thr Gln Met
385                 390

<210> SEQ ID NO 5
<211> LENGTH: 308
<212> TYPE: PRT
<213> ORGANISM: Homo sapiens

<400> SEQUENCE: 5

Met Asp Ala Leu Lys Ser Ala Gly Arg Ala Leu Ile Arg Ser Pro Ser
1               5                   10                  15

Leu Ala Lys Gln Ser Trp Gly Gly Gly Arg His Arg Lys Leu Pro
                20                  25                  30

Glu Asn Trp Thr Asp Thr Arg Glu Thr Leu Leu Glu Gly Met Leu Phe
            35                  40                  45

Ser Leu Lys Tyr Leu Gly Met Thr Leu Val Glu Gln Pro Lys Gly Glu
```

```
              50                  55                  60
Glu Leu Ser Ala Ala Ile Lys Arg Ile Val Ala Thr Ala Lys Ala
 65                  70                  75                  80

Ser Gly Lys Lys Leu Gln Lys Val Thr Leu Lys Val Ser Pro Arg Gly
                 85                  90                  95

Ile Ile Leu Thr Asp Asn Leu Thr Asn Gln Leu Ile Glu Asn Val Ser
                100                 105                 110

Ile Tyr Arg Ile Ser Tyr Cys Thr Ala Asp Lys Met His Asp Lys Val
                115                 120                 125

Phe Ala Tyr Ile Ala Gln Ser Gln His Asn Gln Ser Leu Glu Cys His
            130                 135                 140

Ala Phe Leu Cys Thr Lys Arg Lys Met Ala Gln Ala Val Thr Leu Thr
145                 150                 155                 160

Val Ala Gln Ala Phe Lys Val Ala Phe Glu Phe Trp Gln Val Ser Lys
                165                 170                 175

Glu Glu Lys Glu Lys Arg Asp Lys Ala Ser Gln Glu Gly Gly Asp Val
                180                 185                 190

Leu Gly Ala Arg Gln Asp Cys Thr Pro Ser Leu Lys Ser Leu Val Ala
            195                 200                 205

Thr Gly Asn Leu Leu Asp Leu Glu Glu Thr Ala Lys Ala Pro Leu Ser
210                 215                 220

Thr Val Ser Ala Asn Thr Thr Asn Met Asp Glu Val Pro Arg Pro Gln
225                 230                 235                 240

Ala Leu Ser Gly Ser Ser Val Val Trp Glu Leu Asp Asp Gly Leu Asp
            245                 250                 255

Glu Ala Phe Ser Arg Leu Ala Gln Ser Arg Thr Asn Pro Gln Val Leu
                260                 265                 270

Asp Thr Gly Leu Thr Ala Gln Asp Met His Tyr Ala Gln Cys Leu Ser
            275                 280                 285

Pro Val Asp Trp Asp Lys Pro Asp Ser Ser Gly Thr Glu Gln Asp Asp
            290                 295                 300

Leu Phe Ser Phe
305

<210> SEQ ID NO 6
<211> LENGTH: 2935
<212> TYPE: DNA
<213> ORGANISM: Homo sapiens

<400> SEQUENCE: 6
ggagctggcg ctgggagggg aggagcgcgc agcccgcgcg ccgcagggcc gggcggaaag      60 ttttttcctga cggagttttg gctgcggcag cggcggcggc ggccggagcg ggccatggac    120
gcgctcaagt cggcggggcg ggcgctgatc cggagcccca gcttggccaa gcagagctgg    180
gggggcggtg ccggcaccgg caagctgcct gagaactgga cagacacgcg ggagacgctg    240 ctggaggga tgctgttcag cctcaagtac ctgggcatga cgctagtgga gcagcccaag    300
ggtgaggagc tgtcggccgc cgccatcaag aggatcgtgg ctacagctaa ggccagtggg    360
aagaagctgc agaaggtgac tctgaaggtg tcgccacggg gaattatcct gacagacaac    420
ctcaccaacc agctcattga gaacgtgtcc atatacagga tctcctattg cacagcagac    480
aagatgcacg acaaggtgtt tgcatacatc gcccagagcc agcacaacca gagcctcgag    540
tgccacgcct tcctctgcac caagcggaag atggcacagg ctgttaccct caccgtagcc    600
caggccttca agtcgccctt tgagttttgg caggtgtcca aggaagagaa agagaagagg    660
```

-continued

| | |
|---|---|
| gacaaagcca gccaagaggg aggggacgtc ctggggggccc gccaagactg caccccctcc | 720 |
| ttgaagagct tggtcgccac tgggaacctg ctggacttag aggagacagc taaggccccg | 780 |
| ctgtccacgg tcagcgccaa caccaccaac atggacgagg tgccgcggcc acaagccttg | 840 |
| agtggcagca gtgttgtctg ggagctggat gatggcctgg atgaagcgtt ttcgaggctt | 900 |
| gcccagtctc ggacaaaccc tcaggtcctg gacactggcc tgacagccca ggacatgcat | 960 |
| tacgcccagt gcctctcgcc tgtcgactgg gacaagcctg acagcagcgg cacagagcag | 1020 |
| gatgacctct tcagcttctg agggcccggg gccagccgga cacaagcggc cctgacacgt | 1080 |
| gatggaccaa agccacctgc tgcggggag ccagttctgg ggcccgcctg ccacctctcc | 1140 |
| cagccctcag cattgtcagc ctgaagatca gagctgcagc cagtcaggca ggggagagat | 1200 |
| ttttcttta agccctgctc tttctctgag aaccaaaaga tgccttgaat atttattcag | 1260 |
| tgacttctgg cttatgctca gaagccagtc tgcgtcaggc acgtctcctg ctgcgtgaca | 1320 |
| tgtgcagtgc tgtaatcggc tcccgcttgc tctcctggag caagctctgc cctggctgtg | 1380 |
| ggtatcagga ctgtgaccaa agcatttcta gtcccttctc tctttctaag acccaaatt | 1440 |
| tccctggggg catcctgctt cctgaaagct gttggatttc agtgatttt ccccccaccc | 1500 |
| cccagcacag gagagcaccc acagccgcag aaggggaatg tgtcctcctg ctctgcttcc | 1560 |
| tcagggccca gcaggcgggg gtttgagccc tggaccccag gctcttagag actaaggggc | 1620 |
| agctcctgac caaagacgat acagcttggc actttaaagc attaacagca ggtgtgaccc | 1680 |
| tgagggctcc tccatggtgc tgcattgagt ccagctttcc ttctgccctt cctccaggag | 1740 |
| aaggggccca aggtccccgt ggatggtctc cacctgtgct tggaaccagt gtaactggct | 1800 |
| gctccctgct cccagggact gacacgggga tcatctctgt gaccgccctc cgtcgggccc | 1860 |
| ctgcctgcct tctcccctcc acgcaaggct gtgctcttcc tctggtttct gtgtgtccgt | 1920 |
| ttgagtgtct gcgccccgcc tccccatact tcctgggatg atgtgtgaaa cctgacacct | 1980 |
| agatttattt ggaaatattc tatgaccact ttacagatga ggaaacaggc ctcaagcgtg | 2040 |
| gaggggtaga gtgaagagta gaacccaggt ctgatgccaa agctgctttc ttctctgcct | 2100 |
| cctcctcacg caactcacac ctccttttct tctagctttg ttgtcctccc aggaaccaaa | 2160 |
| aaacccagc tattttctga ccaaaatgtg tttcataaca aaccatctgg tgcctttcca | 2220 |
| cacagaactg gcaggagcct cgtgtcctgc tagctgtctc tcttgttgat ttccgtgaaa | 2280 |
| atgcaagtgt ttgaagtctg ctcattccga gggtgaaaca aaatccaacc ctgtcagaat | 2340 |
| catgctgttc tctttgctga cactgtgacc ctgggtcggg acagaccagc agcaatctgt | 2400 |
| ctttagaatc gctttccttc ctccccttt gccccgtgg ggctcccggc atcctgaaag | 2460 |
| ccagcaaagc ctccagcatc ttttccatcc tgaggtgcct cccagtggcc tggcttgtcg | 2520 |
| gagcaagttt catcagccct agggaaaaca cggccctcct gggaacctcc ttacctggag | 2580 |
| taaccggaca ccttagacgg aggtgcctga ggtgggtg ggatttgcag ggtcattatc | 2640 |
| agaacatgag gataacttcc ttgcccctgc tctgtagcca cctccttggc accggcctct | 2700 |
| atttgtcata aggcggcgtg ggcgaggcct gacacaggcc agccttggca cgaggggggc | 2760 |
| caggggttct gagaagcgct gccctgtgag agccacgctg gccttcgtct ccatctctgg | 2820 |
| ttgacgggct gtccgtgtgc ctcctgtgtg tctgcagaca agtcttgctg tgctttattt | 2880 |
| gtgaaacttt aatgaggaaa aaacaaataa taaatgttct cgttttgaaa ctcaa | 2935 |

<210> SEQ ID NO 7
<211> LENGTH: 186
<212> TYPE: PRT

```
<213> ORGANISM: Homo sapiens

<400> SEQUENCE: 7

Met Asp Ala Leu Lys Ser Ala Gly Arg Ala Leu Ile Arg Ser Pro Ser
1               5                   10                  15

Leu Ala Lys Gln Ser Trp Gly Gly Gly Arg His Arg Lys Leu Pro
                20                  25                  30

Glu Asn Trp Thr Asp Thr Arg Glu Thr Leu Leu Glu Gly Met Leu Phe
                35                  40                  45

Ser Leu Lys Tyr Leu Gly Met Thr Leu Val Glu Gln Pro Lys Gly Glu
            50                  55                  60

Glu Leu Ser Ala Ala Ala Ile Lys Arg Ile Val Ala Thr Ala Lys Ala
65                  70                  75                  80

Ser Gly Lys Lys Leu Gln Lys Val Thr Leu Lys Val Ser Pro Arg Gly
                85                  90                  95

Ile Ile Leu Thr Asp Asn Leu Thr Asn Gln Leu Ile Glu Asn Val Ser
                100                 105                 110

Ile Tyr Arg Ile Ser Tyr Cys Thr Ala Asp Lys Met His Asp Lys Val
            115                 120                 125

Phe Ala Tyr Ile Ala Gln Ser Gln His Asn Gln Ser Leu Glu Cys His
            130                 135                 140

Ala Phe Leu Cys Thr Lys Arg Lys Met Ala Gln Ala Val Thr Leu Thr
145                 150                 155                 160

Val Ala Gln Ala Phe Lys Val Ala Phe Glu Phe Trp Gln Val Ser Lys
                165                 170                 175

Glu Glu Lys Glu Lys Arg Asp Lys Ala Ser
                180                 185

<210> SEQ ID NO 8
<211> LENGTH: 7
<212> TYPE: PRT
<213> ORGANISM: Homo sapiens

<400> SEQUENCE: 8

Tyr Asp Asn Pro Asn Phe Ile
1               5

<210> SEQ ID NO 9
<211> LENGTH: 7
<212> TYPE: PRT
<213> ORGANISM: Rattus norvegicus

<400> SEQUENCE: 9

Tyr Asp Asn Pro Asn Phe Val
1               5

<210> SEQ ID NO 10
<211> LENGTH: 19
<212> TYPE: RNA
<213> ORGANISM: Homo sapiens

<400> SEQUENCE: 10
ccugcuggac uuagaggag                                              19
```

COMPOSITION AND METHOD FOR THE TREATMENT OF HYPERKALEMIA

CROSS REFERENCE TO RELATED APPLICATIONS

This application claims benefit of Provisional Application 61/104,247 filed on Oct. 9, 2008, incorporated herein by reference, under 35 U.S.C. §119(e).

STATEMENT OF GOVERNMENTAL INTEREST

This invention was made with Government support under NIH Grant Nos. DK054231 and DK063049. The Government has certain rights in the invention.

BACKGROUND OF THE INVENTION

1. Field of the Invention

The invention is in the field of methods of treating and preventing potassium imbalance by regulating ROMK endocytosis.

2. Description of Related Art

Pharmacotherapy has progressed rapidly over the last 20 years with the result that general practitioners more and more often use drugs which may influence potassium metabolism at the kidney or gastrointestinal level, or the transmembrane transport of potassium at the cellular level. Potassium abnormalities may result in life-threatening clinical conditions.

Potassium is the most abundant intracellular cation. It is critically important for many physiologic processes, including maintenance of cellular membrane potential, homeostasis of cell volume, and transmission of action potentials in nerve cells. Small changes in the extracellular potassium level can have profound effects on the function of the cardiovascular and neuromuscular systems. Nearly 98% of potassium is intracellular, with the concentration gradient maintained by the sodium- and potassium-activated adenosine triphosphatase ($Na^+/K^+$-ATPase) pump. The normal potassium level is 3.5-5.0 mEq/L, and total body potassium stores are approximately 50 mEq/kg (3500 mEq in a 70-kg person).

Potassium is eliminated through the gastrointestinal tract and the kidney. The kidneys play the major role in maintaining internal body potassium balance. Typically, they excrete 92% of the potassium ingested in the diet. Most importantly, the rate of potassium excretion is regulated in response to changes in dietary intake of potassium. Adaptive regulatory mechanisms ensure that excretion is precisely regulated to be equivalent to intake even when potassium intake increases by as much as 20 times. The primary control over urinary excretion of potassium takes place in the distal tubule and collecting duct system.

Renal elimination of potassium involves filtration, reabsorption, and secretion. Because potassium is unbound in the cell, it is freely filtered by the glomerulus. The proximal tubule then typically reabsorbs about 65% of filtered potassium and Henle's loop reabsorbs another 25%. In both segments, reabsorption is a constant fraction of the amount that was filtered. In contrast, the distal nephron has the dual capacity to both reabsorb and secrete potassium. Furthermore, unlike the proximal tubule and loop of Henle, the rate of potassium reabsorption or secretion in the distal nephron is regulated by hormones, such as aldosterone, and other factors in response to changes in dietary potassium intake.

Minute-to-minute levels of potassium are controlled by intracellular to extracellular exchange, mostly by the sodium-potassium pump that is controlled by insulin and beta2 receptors. A balance of GI intake and renal potassium excretion achieves long-term potassium balance.

Hypokalemia is a condition of low potassium blood levels and is most frequently caused by loss of this electrolyte in the kidney (caused for example by thiazide, thiazide-like and loop diuretics, glucocorticoids) and in the gastrointestinal tract (caused for example by laxatives, diarrhea, vomiting, and external fistula). Hypokalemia can also be the result of an increased intracellular potassium influx induced by sympathicomimetics used mostly by patients with asthma, or by insulin overdosage in diabetic subjects. The leading symptoms of hypokalemia are skeletal and smooth muscle weakness and cardiac arrhythmias.

Hyperkalemia occurs when there is an abnormally elevated blood level of potassium. Extreme degrees of hyperkalemia are considered a medical emergency due to the risk of potentially fatal arrhythmias. One of the causes of hyperkalemia is renal insufficiency. Hyperkalemia may be caused by acute or end-stage renal failure, impaired tubular excretion of potassium, acidemia, and severe cellular injury (tumor lysis syndrome). Medication that interferes with urinary excretion of potassium can also cause hyperkalemia. Such medicines include many commonly prescribed drugs such as ACE inhibitors and angiotensin receptor blockers (ARBs) which are used to treat hypertension; certain potassium-sparing diuretics (e.g. amiloride and spironolactone); NSAIDs such as ibuprofen, naproxen, or celecoxib; immunosuppressants such as cyclosporin and tacrolimus; the antibiotic trimethoprim; and the antiparasitic drug pentamidine. Certain diseases are also associated with hyperkalemia, including Addison's disease, aldosterone deficiency, some forms of congenital adrenal hyperplasia; Type IV renal tubular acidosis (resistance of renal tubules to aldosterone), and Gordon's syndrome ((pseduohypoaldosteronism type II or "familial hypertension with hyperkalemia"), a rare genetic disorder caused by defective modulators of salt transporters. Hyperkalemia can also be caused by rhabdomyolysis, burns or any cause of rapid tissue necrosis, including tumor lysis syndrome, massive blood transfusion or massive hemolysis and transport of potassium ions out of cells caused by acidosis, low insulin levels, beta-blocker therapy, digoxin overdose, or the paralyzing anesthetic succinylcholine. Long term use of these drugs can lead to long term potassium imbalance and secondary hyperkalemia. Hyperkalemia may be the cause of severe injury of both skeletal and smooth muscle cells. The specific treatment counteracting hyperkalemia is a bolus injection of calcium salts and, when necessary, hemodialysis. Kokot F, and Hyla-Klekot L., Pol Arch Med. Wewn. 2008 July-August; 118(7-8):431-4. Patients with the rare hereditary condition of hyperkalemic periodic paralysis appear to have a heightened sensitivity of muscular symptoms that are associated with transient elevation of potassium levels. Episodes of muscle weakness and spasms can be precipitated by exercise or fasting in these subjects.

Current methods of treating hyperkalemia include calcium supplementation, which does not lower potassium but decreases myocardial excitability, protecting against life threatening arrhythmias. Another means of treatment is administration of IV insulin which causes potassium ions to leave the blood and go into cells, as a secondary effect of increased activity of the sodium-potassium ATPase. Bicarbonate therapy is effective in cases of metabolic acidosis, where it stimulates an exchange of cellular hydrogen ions for sodium ions, that in turn stimulates sodium-potassium ATPase. Salbutamol (albuterol, or Ventolin) which is a $\beta_2$-selective catecholamine, can be administered by nebulizer to promote movement of potassium into cells. Another form of treatment is administering polystyrene sulfonate, which is a binding resin that binds potassium in the intestine and removes it from the body by defecation. However, this medication may cause diarrhea. While there are treatments for acute hyperkalemia, there is still a need for long term regulation of potassium balance in subjects who have a genetic predisposition to potassium imbalance, who take drugs that can cause an imbalance, and in patients with chronic renal imbalance to help maintain residual potassium secretion and prolong the time until dialysis is required.

BRIEF DESCRIPTION OF THE DRAWINGS

The present invention is illustrated by way of example, and not by way of limitation, in the figures of the accompanying drawings and in which:

FIG. 6. Mapping the sequence of the endocytotic signal in ROMK. A. Mutations in the putative trafficking signal were created by replacing the endogenously expressed amino acid in each locus of YDN375PNFVL with alanine, and then determining the level of cell surface expression by HA antibody binding and cell surface luminescence in the absence (open bars) and presence of ARH (closed bars). (n=3). B. total cellular input of channel protein was not influenced by ARH.

FIG. 7. Sequence requirements of ARH binding match the requirements for internalization. A. GST-ROMK/His-ARH interaction assay. Western blot analysis with anti-GST antibodies. Mutations of the Y373A, N375A, P376A, F378A and V379A in GST-ROMK blocked most interactions with ARH. B. Quantification of Western blot results. n=3. C. Biotinylation internalization assay to measure endocytosis rate of cell surface mutants at 5 minutes time point. Y373A, N375A, P376A, F378A and V379A mutant Flag-ROMK attenuated endocytosis rate to a level that was statistically different from wide type ROMK channel with the presence of ARH. n=3.

FIG. 8. Dominant-negative (DN) ARH having the amino acid sequence set forth in SEQ ID NO. 7, can abrogate the increase of ROMK endocytosis in the presence of wnk1. A. Right, DN ARH attenuated the level of internalized channel. Left, Quantification of Western blot results. n=3. B. DN ARH rescued the cell surface ROMK expression in the presence of WNK1. Left shows quantification of 3 representative experiments.

SUMMARY OF THE INVENTION

Figure 1:
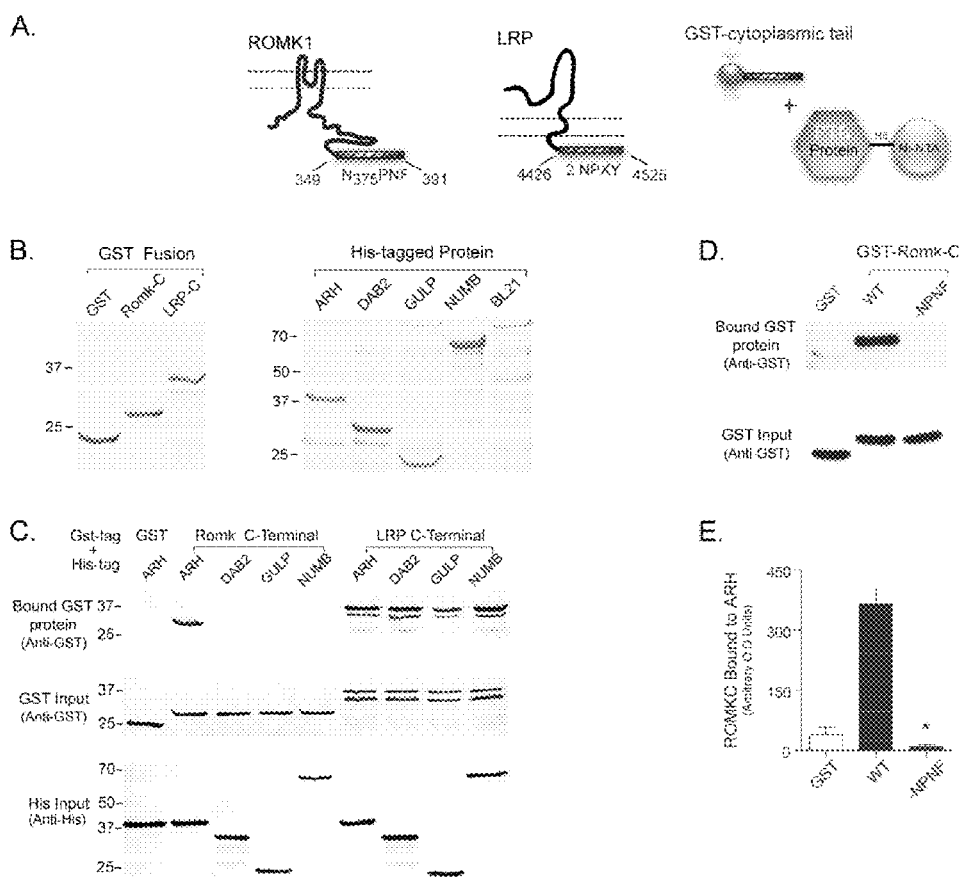
FIG. 1. ROMK specifically interacts with ARH and not other PTB-CLASPs. A. Illustration of the pull down assay. Recombinant His-tagged ARH proteins were purified to homogeneity on Ni-NTA beads and then mixed with purified GST fusion proteins. B. Purified, recombinant GST fusions of the wild-type (WT) ROMK1 C-terminus (amino acids 349-391), LRP C-terminus containing the NPXY motif and His-tagged PTB proteins resolved by SDS-PAGE and visualized by Coomassie Brilliant Blue staining C Western blot analysis with anti-GST antibodies. After incubation, beads were extensively washed and the bound material was subjected to Western blot. The GST-ROMK-C bound to ARH but not other PTB proteins. GST-LRP-C bound to all the PTB proteins as a positive control. D. Quantification of Western blot results. n=3. D-E. ARH interacts with ROMK in an "NPXF" signal dependent manner. A. Western blot analysis with anti-GST antibodies. Mutation of the replacement of the N375PNF sequence with alanine (NPNF was replaced with AAAA) blocked interaction with ARH C. Quantification of Western blot results. n=3.

Certain embodiments of the invention are directed to methods of treating hyperkalemia in a human subject, by administering a therapeutically effective amount of a protein or peptide that is capable of binding to the internalization sequence set forth in SEQ ID NO. 8 on human renal outer medullary potassium channel protein (ROMK) without causing endocytosis. One such protein or peptide comprises a biologically active fragment of human autosomal recessive hypercholesterolemia protein (ARH) or a variant thereof, including fragments lack a clathrin box, or one or both clathrin adaptor AP-2 domains. Another protein that binds to ROMK blocks endocytosis the dominant negative autosomal recessive hypercholesterolemia protein comprising the amino acid sequence set forth in SEQ ID NO. 7 or a biologically active fragment or variant thereof.

Another embodiment is directed to methods of treating hyperkalemia in a human, by administering a therapeutically effective amount of an agent that reduces the expression of ARH or ROMK in kidney cells, including antisense oligonucleotides, siRNA, or microRNA. Expression of ARH can be reduced by administering antisense oligonucleotides that are sufficiently complementary to the gene encoding human ARH set forth in SEQ ID NO. 6 or mRNA encoding human ARH to permit specific hybridization to the gene or mRNA, respectively. Expression of ROMK can be reduced by administering antisense oligonucleotides that are sufficiently complementary to the gene encoding human ROMK set forth in SEQ ID NO. 1 or mRNA encoding human ROMK to permit specific hybridization to the gene or mRNA, respectively. In another embodiment siRNA as set forth in SEQ ID NO. 10 are administered therapeutically to treat hyperkalemia.

Other embodiments of the invention are directed to the peptides YXN375PXFI, wherein X is any amino acid or fragment or variant thereof, preferably YDN375PNFI comprising SEQ ID NO: 8; and YXN375PXFV, wherein X is any amino acid or fragment or variant thereof, preferably YDN375PNFV comprising SEQ ID NO: 9.

DETAILED DESCRIPTION

It was known that the density of constitutively open ROMK channels on the surface of the cortical collecting duct (CCD) principal cell apical membrane are physiologically down-regulated by clathrin-dependent endocytosis in response to dietary potassium deficiency. By contrast, an aberrant overstimulation of ROMK endocytosis contributes to hyperkalemia, for example in pseudohypoaldosteronism type II (hereafter "PHAII"), a familial disorder of diminished renal potassium excretion and hypertension. In PHAII, alterations in WNK1 kinase isoform expression or gain of function mutations in WNK4 have been reported to aberrantly stimulate ROMK endocytosis in model systems, offering one explanation for altered potassium balance in the disease. However, the mechanism by which the density of ROMK channels in the kidney are regulated was not known. The experiments described herein have identified and sequenced the internalization sequence at the C-terminal end of the ROMK protein and have determined that endocytosis is triggered by binding of the ROMK internalization sequence to ARH protein, which is co-localized and expressed with ROMK.

By "ARH" is meant the autosomal recessive hypercholesterolemia (ARH) protein, also referred to in GenBank as the low density lipoprotein receptor adaptor protein 1. The amino acid sequence of human ARH is set forth in SEQ ID NO: 5, and the cDNA sequence is set forth in SEQ ID NO: 6. By "ROMK" is meant the Renal Outer Medullary Potassium channel. This is an ATP-dependent potassium channel (Kir1.1) that transports potassium out of cells. It plays an important role in potassium recycling in the thick ascending limb (TAL) and potassium secretion in the cortical collecting duct (CCD) of the nephron. In humans, ROMK is encoded by the KCNJ1 (potassium inwardly-rectifying channel, subfamily J, member 1) gene.

It has further discovered new methods of treating or preventing hyperkalemia by administering to a patient who is at risk of developing hyperkalemia or who has hyperkalemia, a therapeutically effective amount of an agent that blocks the interaction of the ROMK internalization sequence with ARH protein, thereby preventing or reducing ARH-induced endocytosis of ROMK. An isolated peptide that includes the ROMK internalization sequence or a variant thereof, is such an agent that will bind to endogenous ARH thereby preventing ARH from binding to endogenous ROMK. Another such agent is an ARH protein fragment or a variant of ARH that will compete with endogenous ARH for binding to the internalization sequence on endogenous ROMK without initiating endocytosis. Another therapy for hyperkalemia is administering a therapeutically effective amount of an antisense oligonucleotide or siRNA that down-regulates the expression of ARH, preferably selectively in the kidney.

Converse methods can be used to treat hypokalemia, for example by administering ARH protein or a biologically active fragment or variant thereof that will bind the ROMK internalization sequence to increase ROMK endocytosis, thereby increasing potassium levels.

The Kir1.1 (ROMK) subfamily of inward-rectifying potassium channels are regulated in accordance with the demands of potassium homeostasis to control potassium balance. Expressed on the apical membrane of distal nephron principal cells, these channels provide a final route for renal potassium secretion. Aldosterone, plasma potassium and other factors precisely control ROMK activity, ensuring that potassium excretion precisely matches dietary intake. Because ROMK channels are constitutively open, regulated changes in channel function are largely brought about by alterations in the density of functional channels ROMK at the apical surface. Until now it was not known if this occurred by switching the channel activity on and off, by regulated recruitment and retrieval mechanisms, or a combination of the two processes.

It was known that in states of dietary potassium deficiency, for example, ROMK channels at the apical surface are reduced presumably by endocytosis to limit potassium excretion and maintain potassium balance. However, significantly elevated levels of ROMK endocytosis in the face of normal dietary potassium intake can lead to life-threatening hyperkalemia. Pseduohypoaldosteronism type II (hereafter "PHAII"), a familial disorder of diminished renal potassium excretion and hypertension, is caused by alterations in WNK1 kinase isoform expression or gain of function mutations in WNK4 that aberrantly stimulate ROMK endocytosis in model systems.

Despite its importance to physiology and disease, the molecular mechanisms responsible for ROMK endocytosis were not known until now. A trafficking scaffold, instectin, is believed to recruit the WNK kinases to clathrin-coated pits, but it was unknown how ROMK channels were similarly targeted to sites of endocytic retrieval or how mechanistically WNK affected ROMK endocytosis. A potential clue came from the discovery that mutations in a cytoplasmic C-terminal asparagine, $N^{375}$, dramatically increased ROMK cell surface expression and rendered the channel resistant to WNK kinases. Significantly, $N_{375}$ and the three neighboring residues form the sequence "NPXF," which is similar to the classic canonical "NPXY" internalization signals first discovered in the low density lipoprotein (LDL) receptor. Until now it was believed that the NPXY signal was absolutely required for receptor-mediated endocytosis. Thus ROMK has a new and unique variant of the canonical internalization signal.

Some studies indicated that the conventional endocytotic clathrin adaptor, AP-2, does not directly interact with NPXY signals. Instead, a new and emerging class of adaptor proteins called CLASPS, has recently been implicated. Four of these, Dab-2, Numb, GLUP, and ARH, exhibit a similar modular structure, featuring clathrin-interaction, AP-2-binding sequences and a phosphotyrosine binding domain (PTB domain). Clathrin-coated vesicles are high-capacity carriers that efficiently shuttle numerous cargo proteins or peptides into the cell interior in a generally non-competitive manner (Marks et al., 1996; Santini et al., 1998; Warren et al., 1998). Dab-2 is largely expressed in the proximal tubule where it has been implicated in megalin endocytosis. Numb, a cell fate determinant, has largely been studied in the Notch signal transduction pathways and its role in the kidney is presently unknown. ARH protein, the product of Autosomal Recessive Hypercholesterolemia gene, is known to promote low-density lipoprotein receptor clustering into clathrin-coated pits in hepatocytes, the only other cell type in which ARH protein is known to be expressed. The research to date using RNA analysis has shown that ARH is largely expressed in the liver and kidney, and perhaps also in the spleen and possibly the brain.

ARH Selectively Binds to ROMK in the Distal Nephrons

It has been discovered that ARH selectively binds to ROMK in the distal nephrons. As a first step to explore the involvement of the CLASPs in ROMK endocytosis, all known PTB domain-containing clathrin-adaptor molecules (ARH, Dab 2, GLUP, and Numb) were screened for ROMK binding capacity (FIG. 1A). For these studies a glutathione S-transferase (GST) fusion protein of the extreme C-terminus of ROMK (349-391) was made, containing the "NPXF" motif (Example A). This protein was then purified to homogeneity, and combined with all His-tagged CLASPs. It was then immobilized on Ni-NTA beads (FIG. 1B, Example C). The C-terminal tail of the Low Density Lipoprotein Related Protein Receptor (LRP), containing two canonical NPXY motifs, was also produced as a GST fusion and used as a positive control for CLASP interaction. After extensive washing, material specifically bound to the CLASPs was eluted and subjected to Western blot analysis with anti-GST antibodies (Example H). In contrast to LRP, which bound to all the CLASPs, ROMK specifically interacted with only with ARH. Importantly, alanine-replacement of the NPNF tract in ROMK with the sequence AAAA completely abrogated ARH binding (FIGS. 1D and E), which is consistent with a highly specific endocytotic signal recognition interaction.

Figure 2:
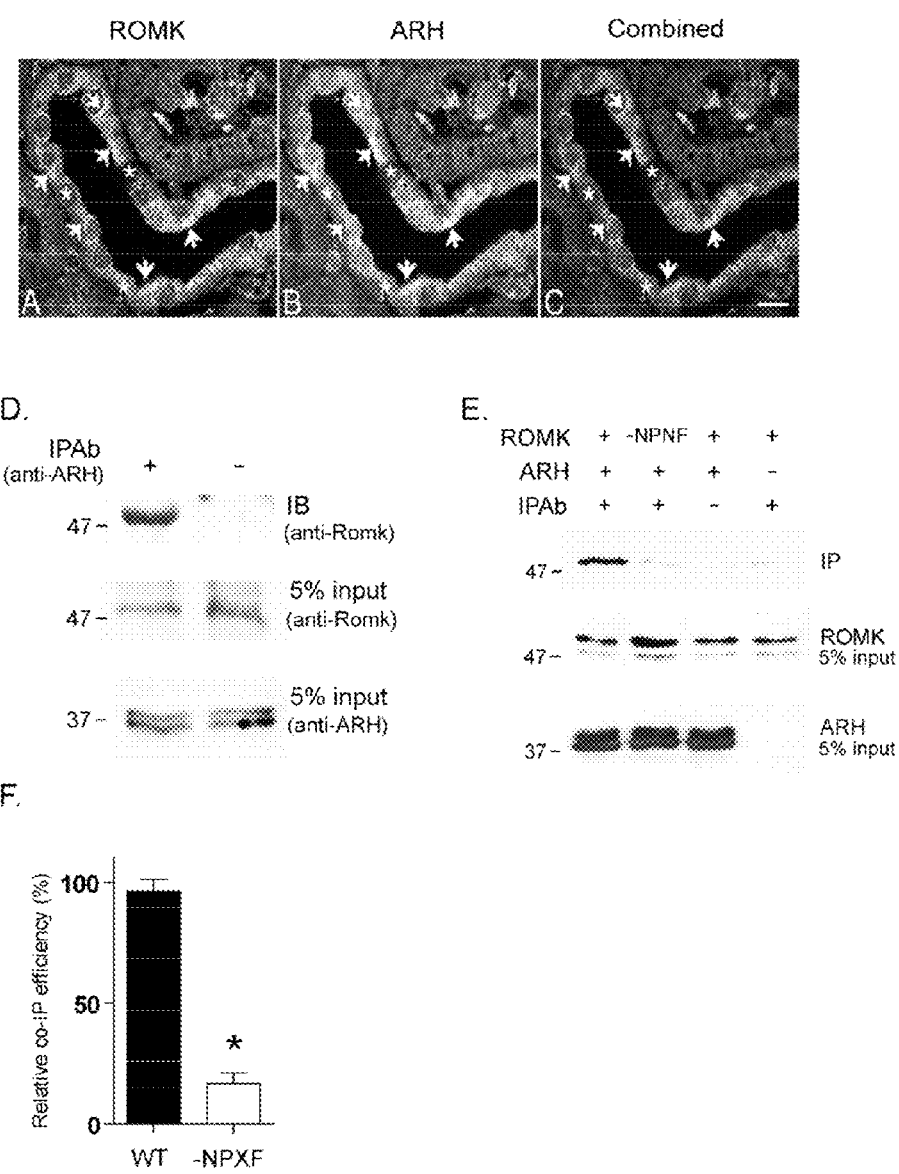
FIG. 2. Colocalization and coimmunoprecipitation of ARH and ROMK in rat kidney collecting ducts Immunofluorescent staining of ARH with goat anti-ARH (Santa Cruz, A), ROMK with chicken anti-ROMK antibody and colocalization of ARH (green) and ROMK (red) using appropriate specific Alexa-conjugated secondary antibodies. Bar=8.5 μm. B. Immunoprecipitation analysis of ROMK channel with ARH from whole rat kidney extracts. IP, immunoprecipitating antibody; IB, immunoblotting antibody C Immunoprecipitation of epitope tagged ROMK or mutant ROMK, lacking the NPXF motif, with myc-tagged ARH from COS-7 cells. Only WT was immunoprecipitated with ARH. D. Quantification of Western blot results. (n=3).

Using immunofluorescent confocal microscopy it was determined that ARH is predominately expressed in the distal nephron, where it co-localizes with ROMK in subapical and perinuclear compartments (FIG. 2A). See Example D. It was also determined that ROMK co-immunoprecipitates with ARH on anti-ARH antibody-bound beads but not with an unrelated IgG (FIG. 2B). The specificity of the ARH-ROMK co-immunoprecipitation was corroborated by similar studies with different antibodies, HA-epitope-tagged ROMK and myc-tagged-ARH in COS-7 cells (FIGS. 2C & D). Importantly, alanine replacement of the NPNF motif in ROMK completely abrogated the ARH-ROMK co-immunoprecipitation.

ARH Facilitates ROMK Endocytosis

Figure 3:
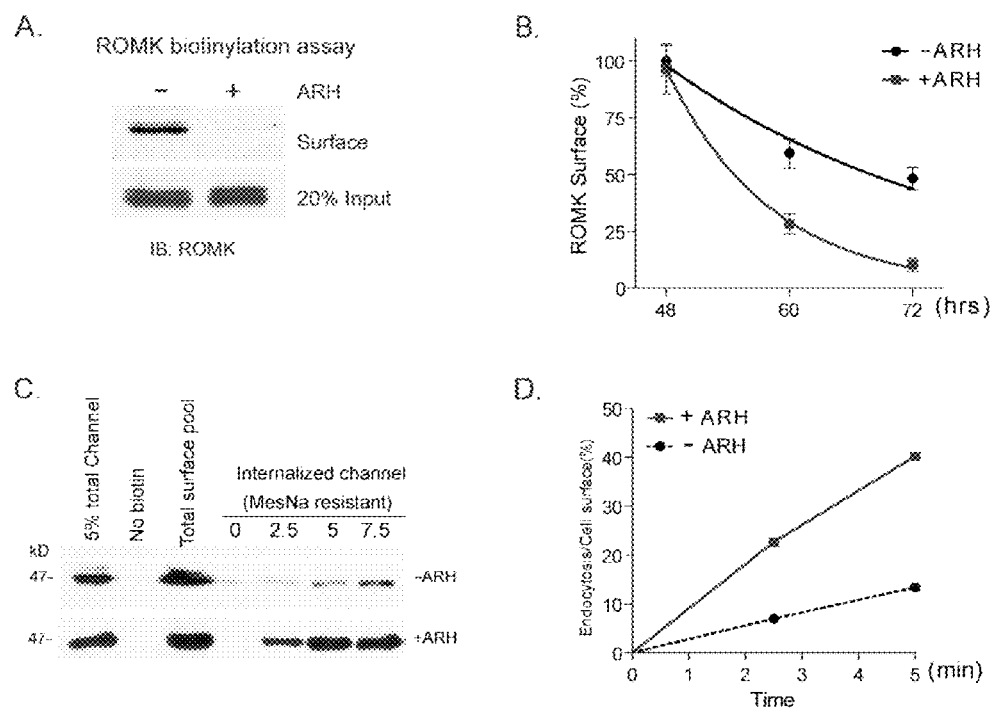
FIG. 3. ARH promotes ROMK endocytosis. A. Cell surface biotinylation of ROMK in COS cells in the absence and presence of ARH. B. Quantification of channel cell surface expression in the absence (open bar) and presence of ARH (closed bar). (n=3). C. ROMK internalization in COS cells in the absence and presence of ARH by biotinylation internalization assay. Surface channels were labeled with sulfo-NHS-SS-biotin in the cold and then incubated at 37° C. to permit trafficking. Biotin remaining at the cell surface was cleaved with MesNa, and internalized (biotinylated) proteins were recovered with neutravidin-conjugated beads and detected along with the total surface pool in immunoblots (IB) with anti-ROMK antibody. No proteins were captured on neutravidin beads without prior biotinylation (second lane). D. Quantification of internalized channel relative to the surface pool at each time point by densitometry (Mean±SE, n=3)

The ability of ARH to interact with ROMK through a C-terminal NPNF signal indicates a capacity to function as an endocytic adaptor. To test whether ARH actually stimulates ROMK endocytosis, surface biotinylation studies were performed in COS-7 cells (Example F). External flag epitope-tagged ROMK channels were labeled at the plasmalemma with a cell-impermeable form of biotin (sulfo-NHS-SS-biotin), recovered on neutravidin beads and then detected using Western blot with anti-ROMK antibodies. It was discovered that co-expression of ARH and ROMK in COS-7 cells led to a dramatic, time-dependent attenuation of ROMK cell surface expression (FIGS. 3A & B) compared to cells that did not express exogenous ARH.

To prove that this attenuation of ROMK cell surface expression was due to augmented endocytosis, dynamic biotinylation studies were performed (Example G). In these studies, cell surface channels were first labeled with sulfo-NHS-SS-biotin at 4° C., and then returned to 37° C. to initiate endocytosis. After variable times, cells were returned to 4° C. and the biotin molecules that remained at the cell surface were stripped with the impermeable reducing agent MesNa. Internalized MesNA-resistant ROMK channel proteins remain biotinylated after MesNa treatment and therefore they can be recovered on neutravidin beads and detected together with the total surface pool (not treated with MesNa) in Western blots with anti-ROMK antibodies (Example H). As shown in a representative experiment (FIG. 3C), increasing amounts of biotinylated channel became resistant to MesNa cleavage over the time course, indicating their internalization via the endocytotic pathway. There was a dramatic and statistically significant increase in internalized ROMK channels over the entire rapid chase period in cells expressing ARH, compared to cells without ARH that were transfected with empty vector (Example I). These results show that ARH stimulates ROMK internalization.

The "sequence listing" below provides the cDNA sequence for human ROMK (SEQ ID NO: 1); the amino acid sequence for human ROMK (SEQ ID NO: 2); the cDNA sequence for *rattus norvegicus* ROMK (SEQ ID NO: 3); the amino acid sequence for *rattus norvegicus* (SEQ ID NO: 4); the amino acid sequence of human ARH protein (which corresponds in GenBank to the low density lipoprotein receptor adaptor protein 1) (SEQ ID NO: 5); the cDNA sequence of the human ARH protein (SEQ ID NO: 6); and the amino acid sequence of dominant negative ARH is shown in SEQ ID NO: 7.

ARH Drives ROMK Endocytosis in a NPNF-Dependent Manner

Figure 4:
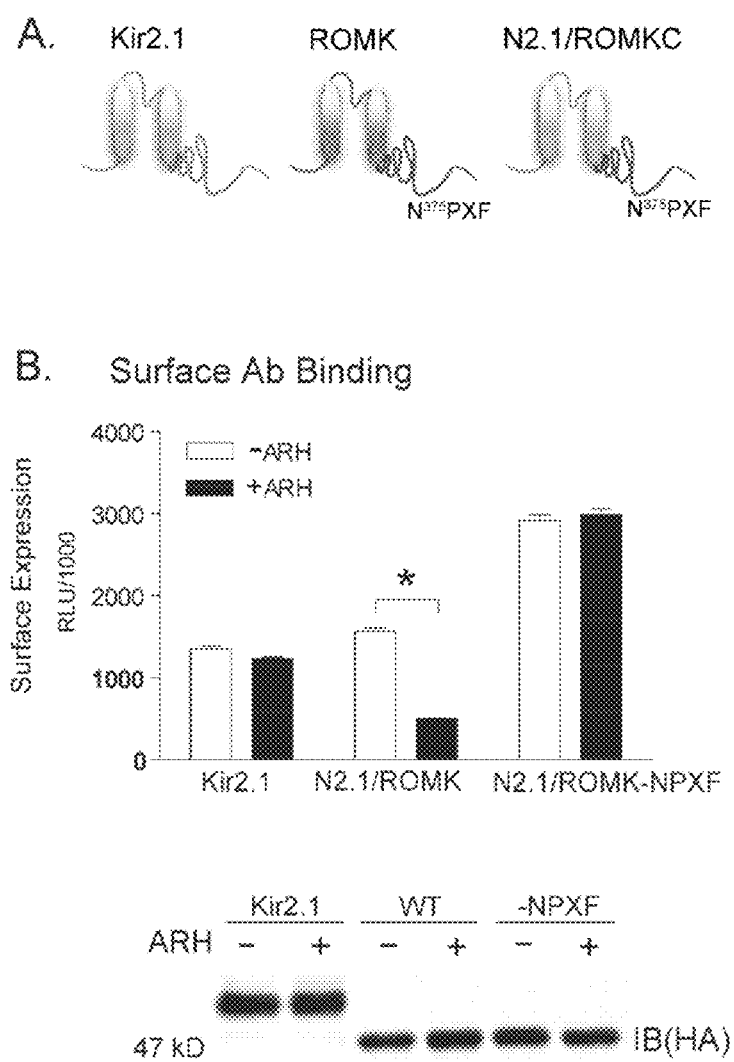
FIG. 4. ARH reduces N2.1/ROMK surface expression in a "NPXF" signal dependent manner. A. Illustrations of the structure of N2.1/ROMK chimera. B. Cell surface HA Ab-binding and luminometry measurements of indicated external HA-tagged channels in COS cells in the absence (open bars) and presence of ARH (closed bars). n=3. Bottom, total cellular input of channel protein is not influenced by ARH.

To examine if ARH stimulates ROMK endocytosis in an NPNF-dependent manner, the NPNF motif was transplanted onto the closely related Kir2.1 channel to create a Kir2.1/ROMK chimera. Kir2.1 shares ~60% amino acid homology with ROMK, but it does not contain either an NPXY or NPXF internalization motif. As measured by cell surface HA-antibody binding in external HA-epitope tagged Kir2.1 cells, it was determined that ARH had no effect on the expression of unmodified, naturally occurring Kir2.1 at the plasmalemma (FIG. 4A). By contrast, modified Kir2.1 channels to which the NPNF motif from ROMK had been added, acquired ARH sensitivity. Indeed, co-expression of ARH with the Kir2.1/ROMK chimera caused a dramatic attenuation of Kir2.1 channel surface expression and a commensurate increase in endocytosis (FIG. 4B).

The result that alanine-replacement of the NPNF tract in ROMK completely abrogated ARH binding (FIGS. 1D and E), is consistent with a highly specific endocytotic signal recognition interaction. In additional experiments the $N_{375}$PNF tract in N2.1/ROMK was replaced with AAAA and discovered that this change increased the surface expression of ROMK by about 100% because it eliminated enough of the internalization sequence that ARH could not bind to ROMK. This result shows that that the NPXF internalization signal in ROMK is the substrate for ARH interaction.

Figure 5:
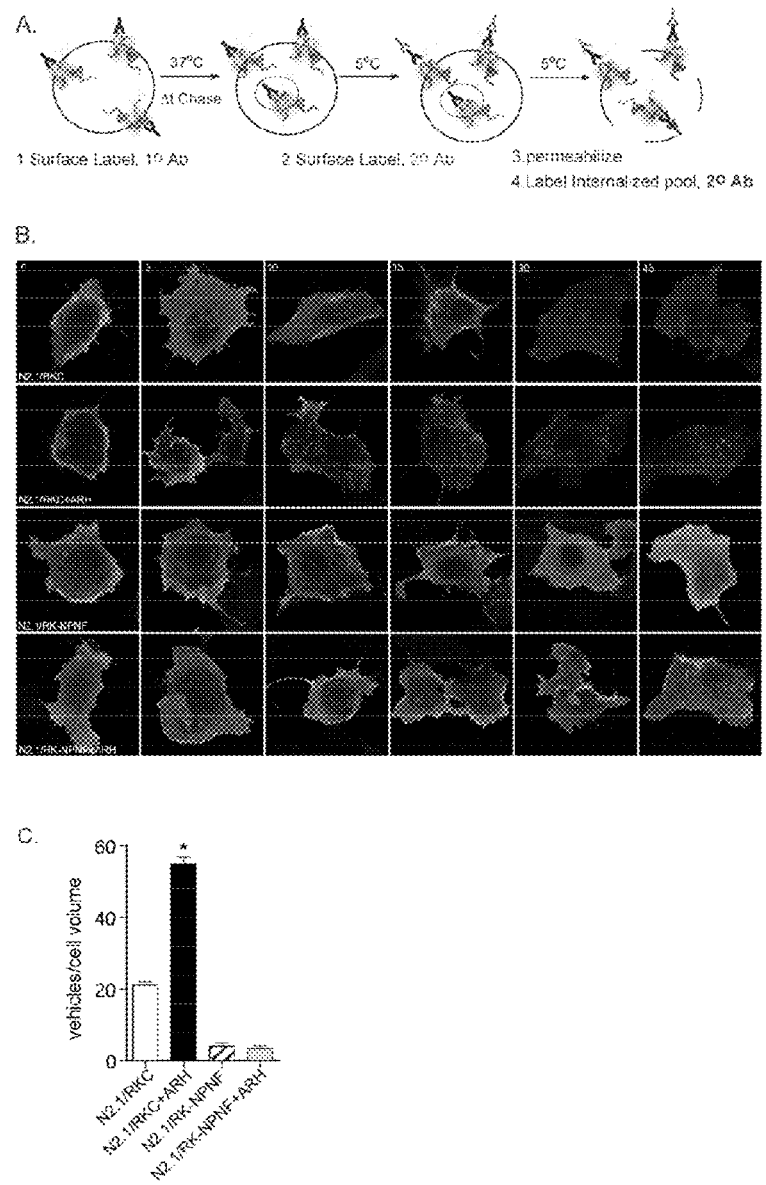
FIG. 5. ARH increases N2.1/ROMK channel internalization in a NPXF signal dependent manner. A. Illustration of antibody feeding assay. B. Representative cells expressing the WT or mutant N2.1/ROMK lacking the NPXF signal in the presence and absence of ARH at time 0, 5, 10, and 15 min at 37° C. Internalized channels are labeled red and surface channels are labeled green using appropriate specific Alexa-conjugated secondary antibodies. Note the increase in red punta in the N2.1/ROMK+ARH cells. C. Quantitative measurements of the intra cellar particles at the 15 minutes time point.

To test whether the suppressive effects of ARH on N2.1/ROMK surface expression were actually due to stimulation of endocytosis, channel internalization was directly measured using an "antibody" feeding assay described in Example D (FIG. 5A). In these studies, live COS-7 cells expressing external HA (hemagglutinin)-epitope-tagged N2.1/ROMK channels, were first incubated with anti-HA antibody in the cold to label the channels at the cell surface, and then shifted to 37° C. to initiate internalization. Following different incubation times at 37° C., the anti-HA-labeled channels that remained on the surface were labeled with saturating amounts of Alexa 488 (green)-conjugated secondary antibody. The internalized fraction of channels, initially labeled at the cell surface with the anti-HA antibody, were labeled with a different secondary antibody, Alexa 568 (red), following cell permeabilization. As shown in FIG. 5B and quantified in 5C, co-expression of ARH lead to a dramatic increase in internalization of N2.1/

ROMK channels. Replacement of the NPXF motif with alanine completely inhibited endocytosis in response to the ARH signal. Taken together, these data provide direct evidence that ARH stimulates ROMK endocytosis in an NPXF dependent manner.

Defining the Precise Sequence of the Internalization Signal.

The experiments described above show that the NPNF sequence functions as part of an internalization sequence, but the precise sequence determinants of ROMK endocytosis and ARH needed to be defined. Initial alanine-cassette mutagenesis studies of a larger region ($R_{371}$-$E_{383}$) encompassing $N_{375}$PNF revealed that flanking residues may also be required for ARH interaction and for ARH-dependent suppression of ROMK surface expression (data not shown). Accordingly, two amino acids at each end of the NPNF motif were included and systemically replaced each individual residue within the YDNPNFVL tract to more precisely define the signature of the $\overline{\text{ROMK}}$ internalization signal. ARH-dependent endocytosis was evaluated by cell surface antibody binding of external HA-epitope tagged channels in COS-7 cells transfected with various mutated forms of ROMK channel and ARH, or empty vector (FIG. 6A). Western blot analysis verified that the mutant channels and ARH were equally expressed (FIG. 6B). Of the eight mutants tested, five (Y373A, N375A, P376A, F378A and V379A) exhibited markedly different phenotypes from the wild type channel, showing an increase in cell surface expression and resistance to the effects of ARH (FIG. 6A). Characterized in this way, it was discovered that the ARH-dependent internalization signal on rat ROMK is defined by the completely novel sequence, YX$N_{375}$PXFV, where x is any amino acid. This internalization sequence is also referred to herein as the "ARH binding site."

Our identification of the YxNPxFV internalization motif in rat ROMK expands the $\overline{\text{spectrum of}}$ "NPXY"-type endocytotic signals. Although ROMK contains the "YxPN" core sequence of the archetypal internalization signal ([Y/F]$_{-3}$x$N_{-2}$$P_{-1}$x$Y_0$), the COOH-end exhibits two noteworthy differences. Replacement of the penultimate tyrosine ($Y_0$) with phenylalanine (F) represents a remarkable departure from the norm. First recognized from an LDL receptor mutation in a familial hypercholesterolemia patient (Davis, C. G. et al. The J.D. mutation in familial hypercholesterolemia: amino acid substitution in cytoplasmic domain impedes internalization of LDL receptors. *Cell* 45, 15-24 (1986)), the tyrosine, $Y_0$, is absolutely conserved in the entire LDL family of receptors Chen, (W. J., Goldstein, J. L. & Brown, M. S, NPXY, a sequence often found in cytoplasmic tails, is required for coated pit-mediated internalization of the low density lipoprotein receptor. *J Biol Chem* 265, 3116-23 (1990)). In fact, with the possible exception of the putative internalization signal in the CD18 subunit of the Human Complement receptor (Rabb, H., Michishita, M., Sharma, C. P., Brown, D. & Arnaout, M. A. Cytoplasmic tails of human complement receptor type 3 (CR3, CD11b/CD18) regulate ligand avidity and the internalization of occupied receptors. *J Immunol* 151, 990-1002 (1993)), it is found in all known "NPXY" signals (Bonifacino, J. S. & Traub, L. M. Signals for sorting of transmembrane proteins to endosomes and lysosomes. *Annu Rev Biochem* 72, 395-447 (2003)). Mutant analysis of the canonical signal in LDLR proteins revealed substitution of $Y_0$ with phenylalanine can variably reduce internalization efficacy (Chen and Paccaud, J. P. et al. Clathrin-coated pit-mediated receptor internalization. Role of internalization signals and receptor mobility. *J Biol Chem* 268, 23191-6 (1993)), depending on the receptor and the structural context of the signal. Strong internalization is maintained in ROMK, despite the natural $Y_0$ to F replacement, likely because the signal is extended a residue, $V_{+1}$. Presumably, this provides an additional source of PTB binding energy as observed with the NAK peptide binding to the Numb PTB domain Li, S. C. et al. Structure of a Numb PTB domain-peptide complex suggests a basis for diverse binding specificity. *Nat Struct Biol* 5, 1075-83 (1998). Together, the two C-terminal deviations in the ROMK signal also may contribute to the tight binding specificity, explaining why ROMK preferentially interacts with ARH while the canonical signal promotes promiscuous PTB-CLASP binding.

The DNA and amino acid sequences of ROMK and ARH protein are highly conserved among mammals. Indeed there is 93% homology between the genes encoding rat and human ROMK and ARH. It was discovered that the amino acid sequence of the internalization sequence/ARH binding site on human ROMK differs by only one amino acid from that in rat. SEQ ID NO. 8 shows the YD$N_{375}$PNFI amino acid sequence of the internalization sequence/ARH binding site on human ROMK and SEQ ID NO. 9 shows the YD$N_{375}$PNFV ARH binding site on rat ROMK. Certain embodiments are directed to these new internalization sequences and to peptides that include them.

The Internalization Motive on ARH Matches the Internalization Sequence on ROMK

If ARH directly interacts with ROMK to mark channels for endocytosis, the internalization motif on ROMK as defined above, should precisely match the interaction motif on ARH. To test this prediction, the "pull down" approach, as described in the examples, was employed to test the sequence requirements for interaction between ROMK and His-tagged ARH. It was directly determined the amount of ROMK channel endocytosis by determining the amount of cell-surface biotinylation. As is shown in FIG. 7, each of the mutations Y373A, N375A, P376A, F378A and V379A, dramatically attenuated binding to ARH (FIG. 7B), and significantly impaired endocytosis (FIG. 7C). This experiment also showed that that the ARH-stimulated internalization sequence on rat ROMK is YXNPXFV, where X is any amino acid; to which certain embodiments are directed.

ARH is Required for WNK-Stimulated ROMK

ROMK endocytosis is regulated by WNK1 in the kidney. To explore whether ARH participates in WNK1-stimulated endocytosis, we developed and tested a dominant negative form of ARH, (herein "DNARH") that contains the PDB domain (amino acids 1-187, SEQ ID. No. 7) but lacks the clathrin box and AP-2 domains.

As measured by biotinylation, the dominant negative ARH protein, a fragment of ARH, almost completely abolished basal—(FIG. 8A) and L-WNK1-stimulated (FIG. 8B) endocytosis. Taken together, these data demonstrate ARH is required for WNK-stimulated ROMK endocytosis. Certain embodiments of the invention are directed to this dominant negative ARH, or to fragments or variants thereof that bind to ROMK without activating endocytosis.

Other splice variants of human ROMK that include the same internalization sequence are identified as:

*Homo sapiens* potassium inwardly-rectifying channel, subfamily J, member 1 (KCNJ1)/ROMK, transcript variant rom-k5, cDNA, NM_153767.2;

NM_153766 *Homo sapiens* potassium inwardly-rectifying channel, subfamily J, member 1 (KCNJ1)/ROMK, transcript variant rom-k4, cDNA, NM_153766.11;

NM_153765 *Homo sapiens* potassium inwardly-rectifying channel, subfamily J, member 1 (KCNJ1)/ROMK, transcript variant rom-k3, cDNA, NM_153765.11;

NM_153764 Homo sapiens potassium inwardly-rectifying channel, subfamily J, member 1 (KCNJ1)/ROMK, transcript variant rom-k2, cDNA, NM_153764.1.

The I to V replacement in human to rat ROMK is also a conservative change (small hydrophobic amino acid substitution) and, thus will not affect its function.

Blocking ROMK endocytosis, specifically in the distal nephron (distal convoluted tubule, connecting tubule, and collecting duct), provides a means to enhance potassium excretion and prevent or reduce hyperkalemia in renal and metabolic disease. For example, this would be of benefit in patients with chronic renal disease, prolonging the time between diagnosis and when dialysis is required. It would also provide a means to alleviate the deleterious side effects of commonly used antihypertensive drugs (e.g. ACE inhibitors, ARBs, minerolocorticoid receptor blockers) on potassium balance.

Stimulating ROMK endocytosis in the distal nephron provides a means to reduce renal potassium excretion to treat or prevent hypokalemia. Important applications include preventing urinary potassium loss with commonly used diuretics and treatment of Bartter's syndrome.

Based on the results of the experiments described above, certain embodiments of the present invention are directed to the newly discovered internalization sequences on mammalian ROMK, including the internalization sequence $YDN_{375}PNFI$ shown in SEQ ID NO: 8 for human ROMK, the internalization sequence $YDN_{375}PNFV$ shown in SEQ ID NO: 9 for rat ROMK; $YXN_{375}PXFI$, where x is any amino acid, $YXN_{375}PXFV$, where x is any amino acid, and to oligonucleotides that encode them. Other embodiments are directed to proteins or peptides that include:
the internalization sequences $YDN_{375}PNFI$ shown in SEQ ID NO: 8 for human ROMK, or
the amino acid sequence $YDN_{375}PNFV$ SEQ ID NO: 9 on rat ROMK, or
$YXN_{375}PXFI$, where x is any amino acid, or
$YXN_{375}PXFV$, where x is any amino acid.

Other embodiments are directed to biologically active fragments or variants of human, rat or other mammalian ROMK that include the respective internalization sequence. Other embodiments are directed to compositions that include the proteins and peptides described above.

Other embodiments are directed to any proteins or peptides that are capable of binding to the internalization sequence on mammalian ROMK without causing endocytosis. These include certain fragments of the ARH protein, preferably fragments that lack the clathrin box, or one or both of the AP-2 domains, or both the clathrin box and one or both of the AP-2 domains. Another such protein is identified herein as the Dominant Negative ARH the amino acid sequence of which is shown in SEQ ID NO: 7.

Other embodiments are directed to various methods of treating or preventing hyperkalemia in a human subject, by administering a therapeutically effective amount of a protein or peptide that binds to endogenous ARH in a way that prevents endogenous ARH from binding to endogenous ROMK and initiating endocytosis. Some of these peptides include YXN375PXFI, wherein X is any amino acid, and fragments or variants thereof. A preferred peptide comprises the internalization sequence on human ROMK which is YDNPNFI, and fragments or variants thereof. Other peptides include $YDN_{375}PNFV$ shown in SEQ ID NO: 9 for rat ROMK, or fragments and variants thereof, and $YXN_{375}PXFV$, where x is any amino acid, and fragments or variants thereof. Any peptide or protein that binds to endogenous ARH and prevents ARH from activating ROMK endocytosis can be used. Some such proteins and peptides may not actually bind to all or even part of the ROMK binding site on ARH, but may alter the conformation of ARH so that the ROMK binding site is blocked, thus preventing ARH from binding to endogenous ROMK. A person of skill in the art can screen the potential therapeutic peptides to preferentially select those that do not bind to unintended targets like low density lipoprotein (LDL) receptor.

Cell-penetrating peptides (CPPs) also called transport proteins or peptides can be used as delivery vehicles for the therapeutic cargo proteins described herein. (see Stewart, K M Org Biomol Chem, '08). CPPs, with appended peptides (i.e. a fusion protein) can promote cellular uptake and in some cases, cell-type specificity. A person of skill in the art will know of methods to optimize delivery of the therapeutic agents of the present invention to the intended target cells in the kidney. For example, proteins and peptides can be delivered intracellularly if conjugated to the protein transduction domain (PTD) of the HIV-1 transcription-activating factor (TAT) (Schwarze S R, Vocero-Akbani A Ho, Dowdy S F. In vivo protein transduction: delivery of a biologically active protein into the mouse. Science. 1999; 285:1569-1572, Zhou Y, Du W, Koretsky T, Bagby G C, Pang Q. TAT-mediated intracellular delivery of NPM-derived peptide induces apoptosis in leukemic cells and suppresses leukemogenesis in mice. Blood. 2008 Sep. 15; 112(6):2474-83, incorporated herein by reference). Hydrophobic biological membranes restrict the passage of hydrophilic molecules such as proteins. However, since TAT translocates across biological membranes, fusion protein constructs with TAT have been used to achieve intracellular delivery of various cargo molecules (Gustafsson A B, Gottlieb R A, Granville D J. TAT-mediated protein transduction: delivering biologically active proteins to the heart. 2005. Methods Mol Med 112:81-90, incorporated herein by reference). The therapeutic agents of the present invention can be fused with transport proteins like TAT for delivery to the intended target cells.

Another method of treating or preventing hyperkalemia includes administering a therapeutically effective amount of an agent that inhibits the expression of ARH in kidney cells such as antisense oligonucleotides, siRNA, and microRNA. In a preferred embodiment the antisense oligonucleotides are complementary to a region of the mRNA or DNA encoding human ARH, and have from about 10 to about 40 consecutive nucleotides. To achieve cell specific expression of RNAi in kidney, the 5'-flanking region of the human AQP2 genes can be used because it contains cis elements that are sufficient for cell-specific expression in the renal collecting duct. (Nelson et al. Am J. Physiol., '98, incorporated herein by reference). This flanking region of AQP2 could be used to suppress gene expression using a vector-based short hairpin RNA (shRNA) by adding it to the siRNA (see Leung et al, Pharmacol Ther. 2005 August; 107(2):222-39).

MicroRNAs (miRNA or μRNA) are single-stranded RNA molecules of about 21-23 nucleotides in length, which regulate gene expression. miRNAs are encoded by genes from whose DNA they are transcribed. MicroRNAs are not translated into protein (i.e. they are non-coding RNAs); instead each primary transcript (a pri-miRNA) is processed into a short stem-loop structure called a pre-miRNA and finally into a functional miRNA. Mature miRNA molecules are partially complementary to one or more messenger RNA (mRNA) molecules, and their main function is to down-regulate gene expression.

Another embodiment is directed to a fragment of the mammalian autosomal recessive hypercholesterolemia (ARH) protein that includes the ROMK binding site, which is useful in drug screening assays, for example to identify agents that interfere with its binding to ROMK.

Other embodiments are directed to various methods for treating or preventing hyporkalemia in a human subject, for example by administering a therapeutically effective amount of the autosomal recessive hypercholesterolemia protein, or a biologically active fragment or variant thereof that is capable of initiating ROMK endocytosis. Other methods include administering agents that interfere with ROMK expression including antisense oligonucleotides, siRNA and microRNAs.

Biologically active fragments and variants of the proteins and peptides as well as modified versions of them are also encompassed by the present invention. The present invention also encompasses vectors comprising nucleic acids encoding the proteins, peptides, and internalization sequences of ROMK described herein.

Certain other embodiments are directed to methods for determining whether a subject is at risk of developing hyperkalemia, by obtaining a biological sample from the subject, and determining if there is a mutation in the region of the ROMK gene encoding the internalization sequence that increases the binding of ROMK to ARH. Alternatively hyperkalemia may be caused by a mutation in the gene encoding the ROMK binding site on ARH that increases the binding of ROMK to ARH thereby increasing endocytosis. Alternatively, a mutation in ARH could interfere with the ability of ARH to bind to ROMK and Activate ROMK endocytosis; a mutation that could cause hypokalemia Antisense Nucleic Acids Some embodiments of the present invention are directed to the use of antisense nucleic acids (either DNA or RNA) or small interfering RNA to reduce or inhibit expression of ARH protein to treat or prevent hyperkalemia. The antisense nucleic acid can be antisense RNA, antisense DNA or small interfering RNA. The amino acid sequence for human ARH is set forth below as SEQ ID NO: 5, and the cDNA sequence is set forth in SEQ ID NO: 6. Based on these known sequences, antisense DNA or RNA that hybridizes specifically to the respective gene or mRNA encoding ARH protein to turn off expression can be readily designed and engineered using methods known in the art. Antisense technology can also be used to reduce expression of ROMK to treat hypokalemia. The cDNA sequence encoding human ROMK is set forth below as SEQ ID NO: 1.

Antisense-RNA and anti-sense DNA have been used therapeutically in mammals to treat various diseases. See for example Agrawal, S, and Zhao, Q. (1998) Curr. Opi. Chemical Biol. Vol. 2, 519-528; Agrawal, S. and Zhang, R. (1997) CIBA Found. Symp. Vol. 209, 60-78; and Zhao, Q, et al., (1998), Antisense Nucleic Acid Drug Dev. Vol 8, 451-458; the entire contents of which are hereby incorporated by reference as if fully set forth herein. Antisense oligodeoxyribonucleotides (antisense-DNA) and oligoribonucleotides (antisense-RNA) can base pair with a gene, or its transcript. An antisense PS-oligodeoxyribonucleotide for treatment of cytomegalovirus retinitis in AIDS patients is the first antisense RNA approved for human use in the US. Anderson, K. O., et al., (1996) Antimicrobial Agents Chemother. Vol. 40, 2004-2011, and U.S. Pat. No. 6,828,151 by Borchers, et al.

Methods of making antisense-nucleic acids are well known in the art. Further provided are methods of modulating the expression of ARH or ROMK protein through the respective gene and mRNA (the sequences of which are known) in cells or tissues by contacting the cells or tissues with one or more of the antisense compounds or compositions of the invention. As used herein, the terms "target nucleic acid" (either encoding ARH or ROMK as needed) encompass DNA encoding ARH protein, RNA (including pre-mRNA and mRNA) transcribed from such DNA, and also cDNA derived from such RNA. The specific hybridization of a nucleic acid oligomeric compound with its target nucleic acid interferes with the normal function of the target nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, and catalytic activity which may be engaged in or facilitated by the RNA. The overall effect of such interference with target nucleic acid function is modulation of the expression of the respective protein. In the context of the present invention, "modulation" means reducing or inhibiting in the expression of the gene or mRNA for ARH protein. cDNA is the preferred antisense nucleotide.

The targeting process includes determination of a site or sites within the target gene or mRNA encoding the ARH or ROMK protein for the antisense interaction to occur such that the desired inhibitory effect is achieved. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene. However routine experimentation will determine the optimal sequence of the antisense or siRNA.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites.

Once one or more target sites have been identified, nucleic acids are chosen which are sufficiently complementary to the target, i.e., hybridize sufficiently well and with sufficient specificity, to give the desired effect of inhibiting gene expression and transcription or mRNA translation.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of a nucleic acid is capable of hydrogen bonding with a nucleotide at the same position of a DNA or RNA molecule, then the nucleic acid and the DNA or RNA are considered to be complementary to each other at that position. The nucleic acid and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the nucleic acid and the DNA or RNA target. Various conditions of stringency can be used for hybridization as is described below. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1 6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2× SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.) high stringency hybridization conditions in 6×SSC at about 45° C., followed by one or more washes in 0.2×SSC, 0.1% SDS at 65° C.; and preferably) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

Antisense nucleic acids have been employed as therapeutic moieties in the treatment of disease states in animals and man. Antisense nucleic acid drugs, including ribozymes, have been safely and effectively administered to humans and numerous clinical trials are presently underway. It is thus established that nucleic acids can be useful therapeutic modalities that can be configured to be useful in treatment regimes for treatment of cells, tissues and animals, especially humans, for example to regulate expression of ARH protein in the kidney.

Nucleic acids in the context of this invention include "oligonucleotides", which refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. \

While antisense nucleic acids are a preferred form of antisense compound, the present invention comprehends other oligomeric antisense compounds, including but not limited to oligonucleotide mimetics. The antisense compounds in accordance with this invention preferably comprise from about 8 to about 50 nucleobases (i.e. from about 8 to about 50 linked nucleosides). Particularly preferred antisense compounds are antisense nucleic acids comprising from about 12 to about 30 nucleobases. Antisense compounds include ribozymes, external guide sequence (EGS) nucleic acids (oligozymes), and other short catalytic RNAs or catalytic nucleic acids which hybridize to the target nucleic acid and modulate its expression.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare nucleic acids such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521, 291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the present invention can be utilized for diagnostics, therapeutics, and prophylaxis and as research reagents and kits.

Small Interfering RNA

US Patent Application 20040023390 (the entire contents of which are hereby incorporated by reference as if fully set forth herein) teaches that double-stranded RNA (dsRNA) can induce sequence-specific posttranscriptional gene silencing in many organisms by a process known as RNA interference (RNAi). However, in mammalian cells, dsRNA that is 30 base pairs or longer can induce sequence-nonspecific responses that trigger a shut-down of protein synthesis and even cell death through apoptosis. Recent work shows that RNA fragments are the sequence-specific mediators of RNAi (Elbashir et al., 2001). Interference of gene expression by these small interfering RNA (siRNA) is now recognized as a naturally occurring strategy for silencing genes in *C. elegans, Drosophila*, plants, and in mouse embryonic stem cells, oocytes and early embryos (Cogoni et al., 1994; Baulcombe, 1996; Kennerdell, 1998; Timmons, 1998; Waterhouse et al., 1998; Wianny and Zernicka-Goetz, 2000; Yang et al., 2001; Svoboda et al., 2000).

In mammalian cell culture, a siRNA-mediated reduction in gene expression has been accomplished by transfecting cells with synthetic RNA nucleic acids (Caplan et al., 2001; Elbashir et al., 2001). The 20040023390 application, the entire contents of which are hereby incorporated by reference as if fully set forth herein, provides exemplary methods using a viral vector containing an expression cassette containing a pol II promoter operably-linked to a nucleic acid sequence encoding a small interfering RNA molecule (siRNA) targeted against a gene of interest.

As used herein RNAi is the process of RNA interference. A typical mRNA produces approximately 5,000 copies of a protein. RNAi is a process that interferes with or significantly reduces the number of protein copies made by an mRNA of the targeted protein, ARH or ROMK. For example, a double-stranded short interfering RNA (siRNA) molecule is engineered to complement and match the protein-encoding nucleotide sequence of the target mRNA to be interfered with. Following intracellular delivery, the siRNA molecule associates with an RNA-induced silencing complex (RISC). The siRNA-associated RISC binds the target mRNA through a base-pairing interaction and degrades it. The RISC remains capable of degrading additional copies of the targeted mRNA. Other forms of RNA can be used such as short hairpin RNA and longer RNA molecules. Longer molecules cause cell death, for example by instigating apoptosis and inducing an interferon response. Cell death was the major hurdle to achieving RNAi in mammals because dsRNAs longer than 30 nucleotides activated defense mechanisms that resulted in non-specific degradation of RNA transcripts and a general shutdown of the host cell. Using from about 20 to about 29 nucleotide siRNAs to mediate gene-specific suppression in mammalian cells has apparently overcome this obstacle. These siRNAs are long enough to cause gene suppression but not of a length that induces an interferon response.

Keyel, et al. describes siRNA that interferes with human ARH protein expression by targeting base pairs 633-651 of the human ARH mRNA nucleotide sequence CCUGCUG-GACUUAGAGGAG SEQ ID NO. 10. This siRNA is available from Qiagen, Valencia, Calif. or Dharmacon, Lafayette, Colo. In a preferred embodiment siRNAs are synthesized with dTdT overhangs and directed against human sequences.

Pharmaceutical Compositions

Based on and supported by the data presented above, certain embodiments of the present invention provide methods for treating or preventing hyper- or hypokalemia. In one embodiment, the method involves administering a therapeutically effective amount of an agent that inhibits or blocks the expression of ARH (hyperkalemia) using such inhibitors as antisense nucleotides, siRNA and microRNAs. Other embodiments include treating or preventing hyperkalemia by administering proteins, or biologically active fragments or variants of them that include all or part of the ROMK internalization sequence that binds to ARH in order to neutralize ARH before it can bind to endogenous ROMK and activate endocytosis. Other such embodiments include administering proteins, or biologically active fragments or variants of them that include all or part of the ROMK binding site on ARH (that binds to ROMK) in order to neutralize endogenous ARH and prevent it from binding to ROMK and initiating endocytosis. One such protein or peptide is the dominant-negative (DN) ARH protein described herein (or fragment or variant thereof). By contrast, hypokalemia can be treated or prevented by administering agents that inhibit ROMK synthesis, or by administering ARH or a biologically active fragment or variant thereof that will bind to ROMK and stimulate endocytosis.

The invention encompasses use of the protein fragments, polypeptides, nucleic acids, and other therapeutic agents described herein formulated in pharmaceutical compositions to administer to a subject, or to target cells or tissues in a subject. Uses are both diagnostic and therapeutic, and for drug screening. The therapeutic agents (also referred to as "active compounds") can be incorporated into pharmaceutical compositions suitable for administration to a subject, e.g., a human. Such compositions typically comprise the nucleic acid molecule, protein or peptide and a pharmaceutically acceptable carrier. It is understood however, that administration can also be to cells in vitro as well as to in vivo model systems such as non-human transgenic animals. Therapeutically, any method known in the art to decrease ARH expression, or inhibit ARH activity, or increase ROMK expression, or block ARH-ROMK complex formation in the kidney can be used to treat or prevent hyperkalemia. By contrast, any method known in the art to increase ARH expression in the kidneys, inhibit ROMK expression, or enhance ARH-ROMK complex formation can be used to treat or prevent hypokalemia.

Formulations of nucleic acids and or peptides may contain more than one active compound as necessary for the particular indication being treated, preferably those with complementary activities that do not adversely affect each other. Such molecules are suitably present in combination in amounts that are effective for the purpose intended.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

A therapeutically effective amount of a protein or polypeptide (i.e., an effective dosage) or nucleic acid (such as antisense nucleotides), is an amount that achieves the desired therapeutic result. For example, a therapeutically effective amount is an amount that ameliorates one or more symptoms of the disease, hyperkalemia or hypokalemia. A therapeutically effective amount of an agent used to treat hyperkalemia is an amount that significantly increases urinary potassium or decreases/normalizes blood potassium levels, and a therapeutically effective amount of an agent that treats hypokelemia is an amount that significantly decreases urinary potassium or increases/normalizes blood potassium. Significantly lower or significantly higher means that the difference is statistically significant.

In one embodiment, the peptides of the present invention are administered daily, weekly or monthly. As a starting point, the therapeutically effective amount comprises a dose from about 0.000001 mg/kg body weight to about 100 mg/kg body weight, preferably a dose of from about 100 ng/day/kg body weight to about 200 mg/day/kg body weight.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease.

The skilled artisan will appreciate that certain factors may influence the dosage required to effectively treat a subject, including but not limited to the severity of the condition, previous treatments, the general health and/or age of the subject, and other disorders or diseases present. Moreover, treatment of a subject with a therapeutically effective amount of a protein, polypeptide, or nucleotide can include a single treatment or, preferably, can include a series of treatments. Appropriate doses also depend upon the potency of the therapeutic agent with respect to the expression or activity to be modulated. When one or more of these small molecules is to be administered to an animal (e.g., a human), a physician, veterinarian, or researcher may, for example, prescribe a relatively low dose at first, subsequently increasing the dose until an appropriate response is obtained.

The actual effective amount of an oligonucleotide or peptide varies according to its size, biodegradability, bioactivity and bioavailability. Optimum dosages can generally be estimated based on $EC_{50}$s found to be effective in in vitro and in vivo animal models. Doses may vary over a wide range from 0.01 micrograms to 100 grams per kg of body weight, and may be given once or more daily, and repeated as needed over weeks, months and even years.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds or therapeutic agents can also be incorporated into the compositions. A pharmaceutical composition of the invention is formulated to be compatible with its intended route of administration.

Examples of routes of administration include parenteral, e.g., intravenous, intradermal, subcutaneous. A person of skill in the art will know which methods will optimize delivery of the active therapeutic agents to the targeted region of the kidney. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylene diamante tetra acetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. Sterile injectable solutions can be prepared by incorporating the active compound (e.g., protein, peptide, antisense nucleotides or siRNA) in the required amount in an appropriate solvent with one or a combination of ingredients enumerated above, as required, followed by filtered sterilization.

In one embodiment, the active compounds are prepared with carriers that will protect the compound against rapid elimination from the body, such as a controlled release formulation, including implants and microencapsulated delivery systems.

Protein Variants.

Variants of ARH or ROMK or fragments thereof, and of the various other peptides described herein include forms that are substantially homologous but derived from another organism, i.e., an ortholog. Variants also include proteins or peptides that are substantially homologous that are produced by chemical synthesis or by recombinant methods.

As used herein, two proteins (or a region of the proteins or peptides) are substantially homologous when the amino acid sequences are at least about 70-75%, typically at least about 80-85%, and most typically at least about 90-95%, 97%, 98% or 99% or more homologous. Variants include conservative Amino Acid Substitutions: Aromatic Phenylalanine Tryptophan Tyrosine Hydrophobic Leucine Isoleucine Valine Polar Glutamine Asparagine Basic Arginine Lysine Histidine Acidic Aspartic Acid Glutamic Acid Small Alanine Serine Threonine Methionine Glycine.

A variant polypeptide can differ in amino acid sequence by one or more substitutions, deletions, insertions, inversions, fusions, and truncations or a combination of any of these. Variant polypeptides can be fully functional or can lack function in one or more activities.

Fully functional variants typically contain only conservative variation or variation in non-critical residues or in non-critical regions. Functional variants can also contain substitution of similar amino acids, which results in no change or an insignificant change in function. Variants of ARH include those that bind to ROMK without causing endocytosis. Alternatively, such substitutions may positively or negatively affect function to some degree.

As indicated, variants can be naturally-occurring or can be made by recombinant means of chemical synthesis to provide useful and novel characteristics of the desired protein. Substantial homology can be to the entire nucleic acid or amino acid sequence or to fragments of these sequences. Fragments can be derived from the full naturally occurring amino acid sequence. However, the invention also encompasses fragments of the variants of ARH as described herein. Accordingly, a fragment can comprise any length that retains one or more of the desired biological activities of the protein, for example the ability to block ARH-ROMK complex formation, or ARH activation of endocytosis. Fragments can be discrete (not fused to other amino acids or polypeptides) or can be within a larger polypeptide. Further, several fragments can be comprised within a single larger polypeptide.

Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described below.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a proprotein sequence.

Protein Modifications

All of the compounds described herein (ARH and ROMK, and biologically active analogs, derivatives, fragments and variants for use in the present invention) and the various peptides described above can be modified according to known methods in medicinal chemistry to increase its stability, half-life, uptake or efficacy. Certain known modifications are described below.

As is also well known, polypeptides are not always entirely linear. For instance, polypeptides may be branched as a result of ubiquitination, and they may be circular, with or without branching, generally as a result of post-translation events, including natural processing events and events brought about by human manipulation which do not occur naturally. Circular, branched and branched circular polypeptides may be synthesized by non-translational natural processes and by synthetic methods.

Modifications can occur anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the amino terminal residue of polypeptides made in E. coli, prior to proteolytic processing, almost invariably will be N-formylmethionine.

The modifications can be a function of how the protein is made. For recombinant polypeptides, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells, and, for this reason, insect cell expression systems have been developed to efficiently express mammalian proteins having native patterns of glycosylation. Similar considerations apply to other modifications. The same type of modification may be present in the same or varying degree at several sites in a given polypeptide. Also, a given polypeptide may contain more than one type of modification.

Some common modifications are set forth below:

| Protein Modification | Description |
| --- | --- |
| Acetylation | Acetylation of N-terminus or e-lysines. Introducing an acetyl group into a protein, specifically, the substitution of an acetyl group for an active hydrogen atom. A reaction involving the replacement of the hydrogen atom of a hydroxyl group with an acetyl group ($CH_3CO$) yields a specific ester, the acetate. Acetic anhydride is commonly used as an acetylating agent, which reacts with free hydroxyl groups. Acylation may facilitate addition of other functional groups. A common reaction is acylation of e.g., conserved lysine residues with a biotin appendage. |
| ADP-ribosylation | Covalently linking proteins or other compounds via an arginine-specific reaction. |
| Alkylation | Alkylation is the transfer of an alkyl group from one molecule to another. The alkyl group may be transferred as an alkyl carbocation, a free radical or a carbanion (or their equivalents). Alkylation is accomplished by using certain functional groups such as alkyl electrophiles, alkyl nucleophiles or sometimes alkyl radicals or carbene acceptors. A common example is methylation (usually at a lysine or arginine residue). |
| Amidation | Reductive animation of the N-terminus. Methods for amidation of insulin are described in U.S. Pat. No. 4,489,159. |
| Carbamylation | Nigen et al. describes a method of carbamylating hemoglobin. |
| Carboxylation | Carboxylation typically occurs at the glutamate residues of a protein, which may be catalyzed by a carboxylase enzyme (in the presence of Vitamin K - a cofactor). |
| Citrullination | Citrullination involves the addition of citrulline amino acids to the arginine residues of a protein, which is catalyzed by peptidylarginine deaminase enzymes (PADs). This generally converts a positively charged arginine into a neutral citrulline residue, which may affect the hydrophobicity of the protein (and can lead to unfolding). |
| Condensation of amines with aspartate or glutamate | Such reactions, may be used, e.g., to attach a peptide to other proteins labels. |
| Covalent attachment of flavin | Flavin mononucleotide (FAD) may be covalently attached to serine and/or threonine residues. May be used, e.g., as a light-activated tag. |
| Covalent attachment of heme moiety | A heme moiety is generally a prosthetic group that consists of an iron atom contained in the center of a large heterocyclic organic ring, which is referred to as a porphyrin. The heme moiety may be used, e.g., as a tag for the peptide. |

| Protein Modification | Description |
| --- | --- |
| Attachment of a nucleotide or nucleotide derivative | May be used as a tag or as a basis for further derivatising a peptide. |
| Cross-linking | Cross-linking is a method of covalently joining two proteins. Cross-linkers contain reactive ends to specific functional groups (primary amines, sulfhydryls, etc.) on proteins or other molecules. Several chemical groups may be targets for reactions in proteins and peptides. For example, Ethylene glycol bis[succinimidylsuccinate, Bis[2-(succinimidooxycarbonyloxy)ethyl]sulfone, and Bis[sulfosuccinimidyl] suberate link amines to amines. |
| Cyclization | For example, cyclization of amino acids to create optimized delivery forms that are resistant to, e.g., aminopeptidases (e.g., formation of pyroglutamate, a cyclized form of glutamic acid). |
| Disulfide bond formation | Disulfide bonds in proteins are formed by thiol-disulfide exchange reactions, particularly between cysteine residues (e.g., formation of cystine). |
| Demethylation | See, e.g., U.S. Pat. No. 4,250,088 (Process for demethylating lignin). |
| Formylation | The addition of a formyl group to, e.g., the N-terminus of a protein. See, e.g., U.S. Pat. Nos. 4,059,589, 4,801,742, and 6,350,902. |
| Glycylation | The covalent linkage of one to more than 40 glycine residues to the tubulin C-terminal tail. |
| Glycosylation | Glycosylation may be used to add saccharides (or polysaccharides) to the hydroxy oxygen atoms of serine and threonine side chains (which is also known as O-linked Glycosylation). Glycosylation may also be used to add saccharides (or polysaccharides) to the amide nitrogen of asparagine side chains (which is also known as N-linked Glycosylation), e.g., via oligosaccharyl transferase. |
| GPI anchor formation | The addition of glycosylphosphatidylinositol to the C-terminus of a protein. GPI anchor formation involves the addition of a hydrophobic phosphatidylinositol group - linked through a carbohydrate containing linker (e.g., glucosamine and mannose linked to phosphoryl ethanolamine residue) - to the C-terminal amino acid of a protein. |
| Hydroxylation | Chemical process that introduces one or more hydroxyl groups (—OH) into a protein (or radical). Hydroxylation reactions are typically catalyzed by hydroxylases. Proline is the principal residue to be hydroxylated in proteins, which occurs at the $C^\gamma$ atom, forming hydroxyproline (Hyp). In some cases, proline may be hydroxylated at its $C^\beta$ atom. Lysine may also be hydroxylated on its $C^\delta$ atom, forming hydroxylysine (Hyl). These three reactions are catalyzed by large, multi-subunit enzymes known as prolyl 4-hydroxylase, prolyl 3-hydroxylase and lysyl 5-hydroxylase, respectively. These reactions require iron (as well as molecular oxygen and α-ketoglutarate) to carry out the oxidation, and use ascorbic acid to return the iron to its reduced state. |
| Iodination | See, e.g., U.S. Pat. No. 6,303,326 for a disclosure of an enzyme that is capable of iodinating proteins. U.S. Pat. No. 4,448,764 discloses, e.g., a reagent that may be used to iodinate proteins. |
| ISGylation | Covalently linking a peptide to the ISG15 (Interferon-Stimulated Gene 15) protein, for, e.g., modulating immune response. |
| Methylation | Reductive methylation of protein amino acids with formaldehyde and sodium cyanoborohydride has been shown to provide up to 25% yield of N-cyanomethyl (—$CH_2CN$) product. The addition of metal ions, such as $Ni^{2+}$, which complex with free cyanide ions, improves reductive methylation yields by suppressing by-product formation. The N-cyanomethyl group itself, produced in good yield when cyanide ion replaces cyanoborohydride, may have some value as a reversible modifier of amino groups in proteins. (Gidley et al.) Methylation may occur at the arginine and lysine residues of a protein, as well as the N- and C-terminus thereof. |
| Myristoylation | Myristoylation involves the covalent attachment of a myristoyl group (a derivative of myristic acid), via an amide bond, to the alpha-amino group of an N-terminal glycine residue. This addition is catalyzed by the N-myristoyltransferase enzyme. |
| Oxidation | Oxidation of cysteines. Oxidation of N-terminal Serine or Threonine residues (followed by hydrazine or aminooxy condensations). Oxidation of glycosylations (followed by hydrazine or aminooxy condensations). |
| Palmitoylation | Palmitoylation is the attachment of fatty acids, such as palmitic acid, to cysteine residues of proteins. Palmitoylation increases the hydrophobicity of a protein. |
| (Poly)glutamylation | Polyglutamylation occurs at the glutamate residues of a protein. Specifically, the gamma-carboxy group of a glutamate will form a peptide-like bond with the amino group of a free glutamate whose alpha-carboxy group may be extended into a polyglutamate chain. The glutamylation reaction is catalyzed by a glutamylase enzyme (or removed by a deglutamylase enzyme). Polyglutamylation has been carried out at the C-terminus of proteins to add up to about six glutamate residues. Using such a reaction, Tubulin and other proteins can be covalently linked to glutamic acid residues. |
| Phospho-pantetheinylation | The addition of a 4'-phosphopantetheinyl group. |
| Phosphorylation | A process for phosphorylation of a protein or peptide by contacting a protein or peptide with phosphoric acid in the presence of a non-aqueous apolar organic solvent and contacting the resultant solution with a dehydrating agent is disclosed e.g., in U.S. Pat. No. 4,534,894. Insulin products are described to be amenable to this process. See, e.g., U.S. Pat. No. 4,534,894. Typically, phosphorylation occurs at the serine, threonine, and tyrosine residues of a protein. |
| Prenylation | Prenylation (or isoprenylation or lipidation) is the addition of hydrophobic molecules to a protein. Protein prenylation involves the transfer of either a farnesyl (linear grouping of three isoprene units) or a geranyl-geranyl moiety to C-terminal cysteine(s) of the target protein. |
| Proteolytic Processing | Processing, e.g., cleavage of a protein at a peptide bond. |
| Selenoylation | The exchange of, e.g., a sulfur atom in the peptide for selenium, using a selenium donor, such as selenophosphate. |
| Sulfation | Processes for sulfating hydroxyl moieties, particularly tertiary amines, are described in, e.g., U.S. Pat. No. 6,452,035. A process for sulphation of a protein or peptide by contacting a protein or peptide with sulphuric acid in the presence of a non-aqueous apolar organic solvent and contacting the resultant solution with a dehydrating agent is disclosed. Insulin products are described to be amenable to this process. See, e.g., U.S. Pat. No. 4,534,894. |
| SUMOylation | Covalently linking a peptide a SUMO (small ubiquitin-related Modifier) protein, for, e.g., stabilizing the peptide. |
| Transglutamination | Covalently linking other protein(s) or chemical groups (e.g., PEG) via a bridge at glutamine residues |
| tRNA-mediated addition of amino acids (e.g., arginylation) | For example, the site-specific modification (insertion) of an amino acid analog into a peptide. |

Drug Screening

Certain embodiments of the invention are directed to cell-based and non-cell based methods of drug screening to identify candidate agents that reduce ARH protein expression in the kidney, or reduce the ability of ARH to initiate endocytosis of ROMK or that block the binding of ARH to ROMK.

The subject assays can be both non-cell based and cell-based. Non-cell based assays for identifying agents that affect gene expression such as antisense or siRNA are very well known. They generally involve (a) contacting a transformed or recombinant cell that has a mutant of a native allele encoding a reporter of gene expression of one (or more) of the various proteins, wherein the expression of the reporter is under the control of the native gene expression regulatory sequences of the native allele, with a candidate agent under conditions whereby but for the presence of the agent, the reporter is expressed at a first expression level; and, (b) measuring the expression of the reporter to obtain a second expression level, wherein a difference between the first and second expression levels indicates that the candidate agent modulates expression of one of the gene.

Libraries of Bioactive Agents (of synthetic or natural compounds) for use in drug screening are known in the art. The term "bioactive agent" or "exogenous compound" as used herein includes any molecule, e.g., protein, oligopeptide, small organic molecule, polysaccharide, polynucleotide, lipid, etc., or mixtures thereof, with the capability of directly or indirectly altering the bioactivity of one of the various proteins or peptides. Bioactive agent agents encompass numerous chemical classes, though typically they are organic molecules, preferably small organic compounds having a molecular weight of more than 100 and less than about 2,500 daltons. Bioactive agent agents comprise functional groups necessary for structural interaction with proteins, particularly hydrogen bonding, and typically include at least an amine, carbonyl, hydroxyl or carboxyl group, preferably at least two of the functional chemical groups. The bioactive agent agents often comprise cyclical carbon or heterocyclic structures and/or aromatic or polyaromatic structures substituted with one or more of the above functional groups. Bioactive agent agents are also found among biomolecules including peptides, saccharides, fatty acids, steroids, purines, pyrimidines, derivatives, structural analogs or combinations thereof. Particularly preferred are peptides.

SEQUENCE LISTING

SEQ ID NO: 1, human ROMK cDNA, Gene Accession No. NM_000220.2, potassium inwardly-rectifying channel, subfamily J, member 1 (KCNJ1), transcript variant rom-k1/ROMK; cDNA

```
GTCTGCATAGAAAGACCAACAACCAGCACCACTTCCTTGCTTTTTCCAGC
CATGAATGCTTCCAGTCGGA

ATGTGTTTGACACGTTGATCAGGGTGTTGACAGAAAGTATGTTCAAACAT
CTTCGGAAATGGGTCGTCAC

TCGCTTTTTTGGGCATTCTCGGCAAAGAGCAAGGCTAGTCTCCAAAGATG
GAAGGTGCAACATAGAATTT

GGCAATGTGGAGGCACAGTCAAGGTTTATATTCTTTGTGGACATCTGGAC
AACGGTACTTGACCTCAAGT

GGAGATACAAAATGACCATTTTCATCACAGCCTTCTTGGGGAGTTGGTTT
TTCTTTGGTCTCCTGTGGTA

TGCAGTAGCGTACATTCACAAAGACCTCCCGGAATTCCATCCTTCTGCCA
ATCACACTCCCTGTGTGGAG

AATATTAATGGCTTGACCTCAGCTTTTCTGTTTTCTCTGGAGACTCAAGT
GACCATTGGATATGGATTCA

GGTGTGTGACAGAACAGTGTGCCACTGCCATTTTTCTGCTTATCTTTCAG
TCTATACTTGGAGTTATAAT

CAATTCTTTCATGTGTGGGGCCATCTTAGCCAAGATCTCCAGGCCCAAAA
AACGTGCCAAGACCATTACG

TTCAGCAAGAACGCAGTGATCAGCAAACGGGGAGGGAAGCTTTGCCTCCT
AATCCGAGTGGCTAATCTCA

GGAAGAGCCTTCTTATTGGCAGTCACATTTATGGAAAGCTTCTGAAGACC
ACAGTCACTCCTGAAGGAGA

GACCATTATTTTGGACCAGATCAATATCAACTTTGTAGTTGACGCTGGGA
ATGAAAATTTATTCTTCATC

TCCCCATTGACAATTTACCATGTCATTGATCACAACAGCCCTTTCTTCCA
CATGGCAGCGGAGACCCTTC

TCCAGCAGGACTTTGAATTAGTGGTGTTTTTAGATGGCACAGTGGAGTCC
ACCAGTGCTACCTGCCAAGT

CCGGACATCCTATGTCCCAGAGGAGGTGCTTTGGGGCTACCGTTTTGCTC
CCATAGTATCCAAGACAAAG

GAAGGGAAATACCGAGTGGATTTCCATAACTTTAGCAAGACAGTGGAAGT
GGAGACCCCTCACTGTGCCA

TGTGCCTTTATAATGAGAAAGATGTTAGAGCCAGGATGAAGAGAGGCTAT
GACAACCCCAACTTCATCTT

GTCAGAAGTCAATGAAACAGATGACACCAAAATGTAACAGTGGCTTTTCA
ACGGGAGTAAAGCAAAGTCT

CTAAAGCTCCTAGTACCTAGAAGCATTATGAAGCAGTCAACAATTTAGGG
GTACGAAAGTAGGATGAGAG

CCTTCAAAGTCTACCAGCACAAAGACCCCTGAGCCCCGCAATTGTGATCC
CACAAGACATGCATCTCCAC

AAGGCTACTGTATTAGAACGTGCAATGCATTTATATGAAACTGGTGTATG
GAAGACATAGGTGCTCTCTT

GAAATCTTAAATATGATTATTTGAGCTCATATAAGGTGGATTGGAGCAGA
TAAAATTATCAAAAGTTTCA

TGAACAGGCCAAACAAAATATTTTTTAAAGTTTCCTTAAAGAAGTTATGA
ACTTTAGAAAGGATCAGGGG

ACAATAATAATCTCATTTTGATTCTACTGATAAGAATGACTCCACTTTTA
ATGTGGACTTTTACTCATGG

AAAAATTGTCTCCTAATTTGGGGAGATGAACCAACCAATCAATGACAAGA
AAACGCTTACACAAAGAACA

ATTTGAGGCTCTAAGCTTCTCATGTGGTACGTTTAGACAGAGGCTAAATC
TGCACACTAGAATCTTGATG

ATACCTTCCTGCAAGACAGAATGCTTTAGTTAAAAGTGGTGATGATATTT
CTTTCAATCTGTATTGGATG

GCTTAAAGGGCTATAAATCTGTTTATAAAGAGCATTTCCTGCTCTTCGAA
GACAGCAATGAGGAGTTGGA

AGGTGCAAAGTCAGTAGAGAAGGGAATGTATCATTAATGCACCTGAGAAG
AAACAGTTTCATGTGTTCCT

CCACCTAGAGTTTGTACTGGAATGCTATTTCTAAAGAAGAAGTGGGAAAG
AGAGAGGAATGGGATGGAGC

CCCACAGTCAGAATGTTACTATGTCTTTCTTTCCCTGACAGCCCATCTTC
CTAAAAGGGACCAGCTTATG

GAAGGCTCGACCTTGAGGGGAAAGTTTTACTGTGAAAGTCTTCTTCAGAT
CCCCACCTGCATCATTCCGA
```

ATGTGTCCTGGAAAAAAACTGGTACTCAAAGCTGCTTAGGAATCAAAATG
TTTTCAGTGTGTTGATTAAT

ATAGTAAATTTCTGAAACTGTG

SEQ ID NO: 2 Human ROMK, Gene Accession No. NP_000211.1 potassium inwardly-rectifying channel J1 isoform a/ROMK; Amino acid sequence

MNASSRNVFDTLIRVLTESMFKHLRKWVVTRFFGHSRQRARLVSKDGRCN

IEFGNVEAQSRFIFFVDIWTTVLDLKWRYKMTIFITAFLGSWFFFGLLWY

AVAYIHKDLPEFHPSANHTPCVENINGLTSAFLFSLETQVTIGYGFRCVT

EQCATAIFLLIFQSILGVIINSFMCGAILAKISRPKKRAKTITFSKNAVI

SKRGGKLCLLIRVANLRKSLLIGSHIYGKLLKTTVTPEGETIILDQININ

FVVDAGNENLFFISPLTIYHVIDHNSPFFHMAAETLLQQDFELVVFLDGT

VESTSATCQVRTSYVPEEVLWGYRFAPIVSKTKEGKYRVDFHNFSKTVEV

ETPHCAMCLYNEKDVRARMKRG<u>YDNPNF</u>ILSEVNETDDTKM

SEQ ID NO:3, *Rattus norvegicus*, Gene Accession No. NM_017023.1, potassium inwardly-rectifying channel, subfamily J, member 1 (Kcnj1)/ROMK; cDNA

CAATCACACAACTCCACTCGAGTTAGCCATTGAAAGCCAATGCAAGTAAA
TGTCATTCCAAAGCTTAAGA

TTCATTAAGGTGGGCCTAAAAGAAGACAGCTGCTGTGCAGACAACGTCGA
ACAAGCACCACTTGCTTGCT

TTGCCCAGCATGGGCGCTTCGGAACGGAGTGTGTTCAGAGTGCTGATCAG
GGCACTGACAGAAAGGATGT

TCAAACACCTCCGAAGATGGTTTATCACTCACATATTTGGGCGTTCCCGG
CAACGGGCAAGGCTGGTCTC

TAAAGAAGGAAGATGTAACATCGAGTTTGGCAATGTGGATGCACAGTCAA
GGTTTATATTCTTTGTGGAC

ATCTGGACAACTGTGCTGGACCTGAAATGGAGGTACAAAATGACCGTGTT
CATCACAGCCTTCTTGGGGA

GTTGGTTCCTCTTTGGTCTCCTGTGGTATGTCGTAGCGTATGTTCATAAG
GACCTCCCAGAGTTCTACCC

GCCTGACAACCGCACTCCTTGTGTGGAGAACATTAATGGCATGACTTCAG
CCTTTCTGTTTTCTCTAGAG

ACTCAAGTGACCATAGGTTACGGATTCAGGTTTGTGACAGAACAGTGCGC
CACTGCCATTTTCCTGCTTA

TCTTCCAGTCTATTCTTGGAGTGATCATCAATTCCTTCATGTGTGGTGCC
ATTTTAGCCAAGATCTCTAG

ACCCAAAAAACGTGCTAAAACCATTACGTTCAGCAAGAATGCGGTGATCA
GCAAGCGTGGCGGGAAGCTC

TGCCTCCTCATCCGAGTGGCCAATCTTAGGAAGAGCCTTCTGATTGGCAG
CCACATATATGGCAAGCTTC

TAAAGACAACCATCACTCCTGAAGGCGAGACCATCATTTTGGATCAGACC
AACATCAACTTTGTCGTCGA

CGCTGGCAATGAAAATTTGTTCTTCATATCCCCACTGACGATCTACCACA
TTATTGACCACAACAGCCCT

TTCTTCCACATGGCAGCAGAAACTCTTTCCCAACAGGACTTTGAGCTGGT
GGTCTTTTTAGATGGCACAG

TGGAATCCACCAGTGCAACCTGCCAGGTCCGCACGTCATACGTCCCAGAG
GAGGTGCTTTGGGGCTACCG

TTTCGTTCCTATTGTGTCCAAGACCAAGGAAGGGAAATACCGAGTTGATT
TTCATAACTTCGGTAAGACA

GTGGAAGTGGAGACCCCTCACTGTGCCATGTGCCTCTATAATGAGAAAGA
TGCCAGGGCCAGGATGAAGA

GAGGCTATGACAACCCTAACTTTGTCTTGTCAGAAGTTGATGAAACGGAC
GACACCCAGATGTAGCAGTG

GCTTTTCCACCTACAAAAAGCCTCCCAAGGACCTAAGGGTTGACTGTGTT
CAGAAGCATCTGACGGGGGT

CTGAAAGCAGGATGAGAACATGCGAAATCTGCTAGCACAGTCACCCCTGA
ACCCCAGGGCTATGGTTCTA

CAAGACACATAGCTCTATAAGGCTGCATACGGTGCATGCATGTGAATGAA
ACTGTGGAAGCCAAAGGGGC

CCACTTGGATCCTCACTATGACTGTGTAAGCTCATATCGTGTTGATGGAA
ACAAAGTCATTCAAGGACAA

AACTTAGGAGCTTTAGAAAGCTTCAGGAACTAGCCACATTTCCTGTTTGA
TTCTATGGATGAGAAGATG

CCATTTTTATCTTAAAGTAGACTTCTATCAATGGAAAATCTGCCCTCTGC
GCTGGGAAGTGAGCCAGCCA

ATCAGTGACAATAAGAGACTGTCATACAAAGAATCAGTAAAGACTCTAAC
CTTCTCAAGCTCTGGTGTTT

GAAGCCTTTGTCTGAGTCTGGGTCCATGCTTCAGAAGGGGTAAGGTGACA
TCCACTGACTGTACCTCTCT

GAACCCAAGGTACAGAAGAACAGGAAGCCCCAATCAACTTCATAATCAAC
CCAGATGCTGCAGCCCATAC

AGAATTTGGCCTGAATGATTTCCTGTGGAGCATTAAATGGAGGCCAAGTC
CACTCTTTAGATATTAAATG

AATATTCTTTTGCAAAGGAAAAAAAAAAAAAAAAAAAAAA

SEQ ID NO: 4, *Rattus norvegicus*, Gene Accession No. NP_058719.1 potassium inwardly-rectifying channel, subfamily J, member 1/ROMK, Amino acid sequence

MGASERSVFRVLIRALTERMFKHLRRWFITHIFGRSRQRARLVSKEGRCN

IEFGNVDAQSRFIFFVDIWTTVLDLKWRYKMTVFITAFLGSWFLFGLLWY

VVAYVHKDLPEFYPPDNRTPCVENINGMTSAFLFSLETQVTIGYGFRFVT

EQCATAIFLLIFQSILGVIINSFMCGAILAKISRPKKRAKTITFSKNAVI

SKRGGKLCLLIRVANLRKSLLIGSHIYGKLLKTTITPEGETIILDQTNIN

FVVDAGNENLFFISPLTIYHIIDHNSPFFHMAAETLSQQDFELVVFLDGT

VESTSATCQVRTSYVPEEVLWGYRFVPIVSKTKEGKYRVDFHNFGKTVEV

ETPHCAMCLYNEKDARARMKRG<u>YDNPNF</u>VLSEVDETDDTQM

SEQ ID NO. 5
Human Protein Sequence of (GenBank) low density lipoprotein receptor adaptor protein 1 which is referred to herein as ARH Protein.
NP_056442

<u>MDALKSAGRALIRSPSLAKQSWGGGGRHRKLPENWTDTRETLLEGMLFSL</u>

<u>KYLGMTLVEQPKGEELSAAAIKRIVATAKASGKKLQKVTLKVSPRGIILT</u>

<u>DNLTNQLIENVSIYRISYCTADKMHDKVFAYIAQSQHNQSLECHAFLCTK</u>

<u>RKMAQAVTLTVAQAFKVAFEFWQVSKEEKEKRDKASQEGGDVLGARQDCT</u>

-continued
PSLKSLVATGNLLDLEETAKAPLSTVSANTTNMDEVPRPQALSGSSVVWE

LDDGLDEAFSRLAQSRTNPQVLDTGLTAQDMHYAQCLSPVDWDKPDSSGT

EQDDLFSF

**The amino acid sequence of the dominant recessive ARH (underlined above) corresponds to amino acids 1-187 of full length human ARH; see SEQ ID NO: 7 below.

SEQ ID NO: 6

| NM_015627 | 2935 bp | cDNA | linear |
|---|---|---|---|

DEFINITION *Homo sapiens* (GenBank) low density lipoprotein receptor adaptor protein 1 which is referred to herein as ARH Protein.

GGAGCTGGCGCTGGGAGGGGAGGAGCGCGCAGCCCGCGCGCCGCAGGGCC
GGGCGGAAAGTTTTTCCTGA

CGGAGTTTTGGCTGCGGCAGCGGCGGCGGCGCCGGAGCGGGCCATGGAC
GCGCTCAAGTCGGCGGGGCG

GGCGCTGATCCGGAGCCCCAGCTTGGCCAAGCAGAGCTGGGGGGGCGGTG
GCCGGCACCGCAAGCTGCCT

GAGAACTGGACAGACACGCGGGAGACGCTGCTGGAGGGGATGCTGTTCAG
CCTCAAGTACCTGGGCATGA

CGCTAGTGGAGCAGCCCAAGGGTGAGGAGCTGTCGGCCGCCGCCATCAAG
AGGATCGTGGCTACAGCTAA

GGCCAGTGGGAAGAAGCTGCAGAAGGTGACTCTGAAGGTGTCGCCACGGG
GAATTATCCTGACAGACAAC

CTCACCAACCAGCTCATTGAGAACGTGTCCATATACAGGATCTCCTATTG
CACAGCAGACAAGATGCACG

ACAAGGTGTTTGCATACATCGCCCAGAGCCAGCACAACCAGAGCCTCGAG
TGCCACGCCTTCCTCTGCAC

CAAGCGGAAGATGGCACAGGCTGTTACCCTCACCGTAGCCCAGGCCTTCA
AAGTCGCCTTTGAGTTTTGG

CAGGTGTCCAAGGAAGAGAAAGAGAAGAGGGACAAAGCCAGCCAAGAGGG
AGGGGACGTCCTGGGGGCCC

GCCAAGACTGCACCCCCTCCTTGAAGAGCTTGGTCGCCACTGGGAACCTG
CTGGACTTAGAGGAGACAGC

TAAGGCCCCGCTGTCCACGGTCAGCGCCAACACCACCAACATGGACGAGG
TGCCGCGGCCACAAGCCTTG

AGTGGCAGCAGTGTTGTCTGGGAGCTGGATGATGGCCTGGATGAAGCGTT
TTCGAGGCTTGCCCAGTCTC

GGACAAACCCTCAGGTCCTGGACACTGGCCTGACAGCCCAGGACATGCAT
TACGCCCAGTGCCTCTCGCC

TGTCGACTGGGACAAGCCTGACAGCAGCGGCACAGAGCAGGATGACCTCT
TCAGCTTCTGAGGGCCCGGG

GCCAGCCGGACACAAGCGGCCCTGACACGTGATGGACCAAAGCCACCTGC
TGCGGGGAGCCAGTTCTGG

GGCCCGCCTGCCACCTCTCCCAGCCCTCAGCATTGTCAGCCTGAAGATCA
GAGCTGCAGCCAGTCAGGCA

GGGGAGAGATTTTTCTTTTAAGCCCTGCTCTTTCTCTGAGAACCAAAAGA
TGCCTTGAATATTTATTCAG

TGACTTCTGGCTTATGCTCAGAAGCCAGTCTGCGTCAGGCACGTCTCCTG
CTGCGTGACATGTGCAGTGC

TGTAATCGGCTCCCGCTTGCTCTCCTGGAGCAAGCTCTGCCCTGGCTGTG
GGTATCAGGACTGTGACCAA

AGCATTTCTAGTCCCTTCTCTCTTTCTAAGGACCCAAATTTCCCTGGGGG
CATCCTGCTTCCTGAAAGCT

GTTGGATTTCAGTGATTTTTCCCCCCACCCCCCAGCACAGGAGAGCACCC
ACAGCCGCAGAAGGGGAATG

TGTCCTCCTGCTCTGCTTCCTCAGGGCCCAGCAGGCGGGGGTTTGAGCCC
TGGACCCCAGGCTCTTAGAG

ACTAAGGGGCAGCTCCTGACCAAAGACGATACAGCTTGGCACTTTAAAGC
ATTAACAGCAGGTGTGACCC

TGAGGGCTCCTCCATGGTGCTGCATTGAGTCCAGCTTTCCTTCTGCCCTT
CCTCCAGGAGAAGGGGCCCA

AGGTCCCCGTGGATGGTCTCCACCTGTGCTTGGAACCAGTGTAACTGGCT
GCTCCCTGCTCCCAGGGACT

GACACGGGATCATCTCTGTGACCGCCCTCCGTCGGGCCCCTGCCTGCCT
TCTCCCCTCCACGCAAGGCT

GTGCTCTTCCTCTGGTTTCTGTGTGTCCGTTTGAGTGTCTGCGCCCCGCC
TCCCCATACTTCCTGGGATG

ATGTGTGAAACCTGACACCTAGATTTATTTGGAAATATTCTATGACCACT
TTACAGATGAGGAAACAGGC

CTCAAGCGTGGAGGGGTAGAGTGAAGAGTAGAACCCAGGTCTGATGCCAA
AGCTGCTTTCTTCTCTGCCT

CCTCCTCACGCAACTCACACCTCCTTTTCTTCTAGCTTTGTTGTCCTCCC
AGGAACCAAAAAACCCCAGC

TATTTTCTGACCAAAATGTGTTTCATAACAAACCATCTGGTGCCTTTCCA
CACAGAACTGGCAGGAGCCT

CGTGTCCTGCTAGCTGTCTCTCTTGTTGATTTCCGTGAAAATGCAAGTGT
TTGAAGTCTGCTCATTCCGA

GGGTGAAACAAAATCCAACCCTGTCAGAATCATGCTGTTCTCTTTGCTGA
CACTGTGACCCTGGGTCGGG

ACAGACCAGCAGCAATCTGTCTTTAGAATCGCTTTCCTTCCTCCCCTTTT
GCCCCCGTGGGGCTCCCGGC

ATCCTGAAAGCCAGCAAAGCCTCCAGCATCTTTTCCATCCTGAGGTGCCT
CCCAGTGGCCTGGCTTGTCG

GAGCAAGTTTCATCAGCCCTAGGGAAAACACGGCCCTCCTGGGAACCTCC
TTACCTGGAGTAACCGGACA

CCTTAGACGGAGGTGCCTGAGGGTGGGTGGGATTTGCAGGGTCATTATC
AGAACATGAGGATAACTTCC

TTGCCCCTGCTCTGTAGCCACCTCCTTGGCACCGGCCTCTATTTGTCATA
AGGCGGCGTGGGCGAGGCCT

GACACAGGCCAGCCTTGGCACGAGGGGGGCCAGGGGTTCTGAGAAGCGCT
GCCCTGTGAGAGCCACGCTG

GCCTTCGTCTCCATCTCTGGTTGACGGGCTGTCCGTGTGCCTCCTGTGTG
TCTGCAGACAAGTCTTGCTG

TGCTTTATTTGTGAAACTTTAATGAGGAAAAAACAAATAATAAATGTTCT
CGTTTTGAAACTCAA

SEQ ID NO. 7 Dominant negative ARH amino acid sequence; 187 amino acids in length.

MDALKSAGRALIRSPSLAKQSWGGGGRHRKLPENWTDTRETLLEGMLFSL

KYLGMTLVEQPKGEELSAAAIKRIVATAKASGKKLQKVTLKVSPRGIILT

DNLTNQLIENVSIYRISYCTADKMHDKVFAYIAQSQHNQSLECHAFLCTK

RKMAQAVTLTVAQAFKVAFEFWQVSKEEKEKRDKAS

SEQ ID NO. 8 shows YDN$_{375}$PNFI amino acid sequence of the internalization sequence/ARH binding site on human ROMK SEQ ID NO. 9 shows the YDN$_{375}$PNFV amino acid internalization sequence/ARH binding site on rat ROMK.

In the foregoing specification, the invention has been described with reference to specific embodiments. It will, however, be evident that various modifications and changes may be made without departing from the broader spirit and scope of the invention. The specification and drawings are, accordingly, to be regarded in an illustrative rather than a restrictive sense. The contents of all references, pending patent applications and published patents, cited throughout this application are hereby expressly incorporated by reference as if set forth herein in their entirety, except where terminology is not consistent with the definitions herein. Although specific terms are employed, they are used as in the art unless otherwise indicated.

EXAMPLES

Experimental Procedures

A. Molecular Biology—All studies were performed with the modified rat ROMK1, containing an external hemagglutinin (HA) epitope tag as described before. Site-directed mutagenesis was performed using a PCR-based strategy with PfuTurbo DNA polymerase (QuikChange, Stratagene). The sequence of all modified cDNAs was confirmed by dye termination DNA sequencing (University of Maryland School of Medicine Biopolymer Core). cDNAs encoding ROMK1 cytoplasmic COOH(C)-terminal regions (amino acids 349-391) were amplified by PCR from a full-length template (GenBank NM_017023) and cloned in-frame with GST in the fusion expression vector pGEX-5x (Amersham Biosciences). Adaptor proteins (ARH, DAB2, GULP, NUMB) whole length or fragment containing PTB domain were cloned into pRSET vector (Invitrogen) as His-tagged fusion proteins. All constructs used for mammalian expression were subcloned into pcDNA 3.1+ (Invitrogen). GST LRP C-terminal expressing vector was generously provided by Dr. Dudley K Strickland from University of Maryland.

B. Cell Culture, Transfection, Lysis and Rat Kidney Homogenization—Monkey COS-7 cells were cultured in a humidified atmosphere at 37° C. in 5% $CO_2$ and grown in Dulbecco's modified Eagle's medium supplemented with 10% fetal bovine serum (FBS), 100 units/ml penicillin, 100 μg/ml streptomycin, 10 mM HEPES, and 2 mM L-glutamine Cells were transfected with 1-2 μg of plasmid using FuGENE 6 reagent (Roche Applied Science) according to the manufacturer's specifications.

Cells were washed once in Ringer's solution, harvested in HEENG buffer (20 mM HEPES, pH 7.6, 25 mM NaCl, 1 mM EDTA, 1 mM EGTA, 10% glycerol) and resuspended in HEENG containing 1% Triton X-100 and protease inhibitors. Cell lysates were resuspended by pipetting, incubated on ice for 45 minutes, and centrifuged at maximum speed to pellet insoluble material. Isolated whole kidneys were resuspended in HEENG buffer containing protease inhibitor cocktail and 1% Triton X-100 and homogenized using the Polytron (PT 10-35) tissue homogenizer. Protein concentrations were assessed by Bradford Assay Reagent (BioRad).

C. GST Affinity Chromatography—GST-ROMK C-terminal fusion proteins and His-PTB adaptor proteins were produced in *Escherichia coli* (BL21, Invitrogen), and purified under nondenaturing conditions using glutathione-Sepharose 4B affinity chromatography (Amersham Biosciences) or TALON® Metal Affinity Resins (Clontech) as recommended by the manufacturers, respectively. Aliquots of Ni-NTA beads containing 2-5 μg of the recombinant His-tagged adaptor proteins were mixed with an equal quantity of each GST fusion protein in 300 μl of binding buffer (20 mM HEPES, 20 mM imidazole, 120 mM potassium acetate, and 0.1% Triton X-100, pH 7.5) and incubated for 45 min on a rotating platform at 4° C. Beads were collected by centrifugation (5000 rpm for 5 min), and the supernatants were removed by aspiration and stored. Beads were washed three times with 1 ml binding buffer each time. Protein bound to beads was eluted in SDS-sample buffer, resolved by SDS-PAGE, and then processed for Coomassie blue staining (Bio-Rad) or for immunoblotting. For the latter, proteins were transferred electrophoretically to nitrocellulose membrane (Hybond, Amersham Biosciences) and probed with either a goat polyclonal anti-GST antibody (GE) at 1:1000 or a rabbit polyclonal anti-His (SANTA CRUZ) antibody followed by horseradish peroxidase (HRP)-conjugated secondary antibody (either mouse anti-goat IgG or goat-anti rabbit IgG at 1:5,000 (Jackson Laboratory).

D. Immunofluorescence, Confocal Microscopy and Antibody Feeding Assay—Cells, grown on glass coverslips, were transfected as above. For colocalization studies of HA-ROMK2 and Myc-tagged ARH, cells were fixed with 4% formaldehyde in PBS buffer for 15 min at 4° C., then permeabilized with 0.1% Triton X-100 for 10 min at room temperature (RT) and washed three times in PBS buffer before blocking (5% bovine serum albumin in the PBS buffer for 30 min at RT). Next, cells were labeled with primary antibodies (mouse anti-HA from Covance and Rabbit anti-Myc from SANTA CRUZ) in 5% bovine serum albumin for overnight at 4° C. Cells were washed in PBS buffer three times and incubated with secondary antibodies conjugated to either ALEXA 488 (goat anti-mouse, Molecular Probes) or ALEXA 568 (goat anti-Rabbit, Molecular Probes) in PBS buffer with 5% bovine serum albumin for 10 min at RT in the dark. Slides were then washed and mounted onto slides in VectaShield (Vector Laboratories) and sealed with nail polish. Cells were visualized using a Zeiss 410 laser scanning confocal microscope under a 63× oil immersion lens. For the external HA-tagged N2.1/ROMKC antibody feeding studies, cells were washed in ice-cold PBS buffer after 2 days of transfection and surface channels were labeled with anti-HA antibody (Covance) at 4° C. for 1 hr. Then cells were quickly washed by cold PBS three times to remove the unbound antibodies and surface channels were internalized at 37° C. for different time points. The extracellular channels were then labeled with Alexa-488-conjugated goat anti-mouse secondary antibody. Following permeabilization with 0.1% Triton X-100 for 10 min at RT, the internalized channels were labeled with Alexa-568-conjugated goat anti-mouse secondary antibody. After extensive washing with PBS buffer, the coverslips were mounted on the glass slide with Vectashield. The labeled cells were visualized under Zeiss 410 confocal microscopy. Images were processed by Adobe Photoshop and analyzed by Volocity (Improvision Inc.).

E. Cell Surface Expression Assay—Channel surface expression in oocytes was quantified by chemiluminescence as described previously. To quantify the cell surface expression in mammalian cells, COS-7 cells were plated on 6-well tissue culture dishes and transfected with 1 μg of plasmid DNA using FuGENE6 reagent (Roche) at a 50-60% cell confluence. After 48 hours, transfected cells were incubated on ice with blocking buffer (5% FBS in PBS buffer) for 30 min, then incubated with mouse monoclonal anti-HA antibody (Covance), washed with PBS buffer 3 times for 5 min each time, incubated with goat anti-mouse IgG HRP-conjugated secondary antibody (Jackson), and extensively washed (PBS buffer 5 min/time for 3 times). The cells were scraped from the plates and resuspended into 500 µl PBS buffer. 10 µl of cell suspension was incubated with 100 µl of mixed Supersignal West Pico Chemiluminescent solution (Pierce), and then chemiluminescence was measured by a Sirius luminometer after 5 min of incubation. Reported values represent the average of triplicate transfections.

F. Biotinylation Internalization Assay—Cells were washed with ice cold Ringer's solution (5 mM HEPES, 144 mM NaCl, 5 mM KCl, 1.2 mM $NaH_2PO_4$, 5.5 mM glucose, 1 mM $MgCl_2$, 1 mM $CaCl_2$, pH 7.4), and the surface proteins were biotinylated using EZ-link Sulfo-NHS-SS-Biotin (0.3 mg/ml, Pierce) in Ringer's solution for 1 hour at 4° C. Remaining biotin was quenched with 50 mM Tris, pH 7.5 in Ringer's solution for 20 minutes at 4° C. Cells were then placed at 37° C. for the indicated amount of time to allow internalization. The membrane-impermeable reducing agent MesNa (100 mM MesNa, 100 mM NaCl, 1 mM EDTA, 0.2% BSA, 50 mM Tris, pH 8.8) was added three times for 20 minutes at 4° C. to cleave biotin linked to the cell surface. Cells were then washed three times with Ringer's solution and lysed. 100 µg of total protein was added to neutravidin beads (Pierce) in PBS buffer containing 0.1% SDS and rotated overnight at 4° C. Beads were washed three times with PBS buffer plus 0.1% SDS and biotinylated protein was eluted from the beads with 6×SDS sample buffer (45 minutes at RT). Proteins were resolved by SDS-PAGE and subject to western blot analysis.

G. Biotinylation cell surface channel Assay—Cell surface channel was biotinylated as above, remaining biotin was quenched with 50 mM Tris, pH 7.5 in Ringer's solution for 20 minutes at 4° C. Cells were then washed three times with Ringer's solution and lysed. 100 µg of total protein was added to neutravidin beads in PBS buffer containing 0.1% SDS and rotated overnight at 4° C. Beads were washed three times with PBS buffer plus 0.1% SDS and biotinylated protein was eluted from the beads with 6×SDS sample buffer (45 minutes at RT). Proteins were resolved by SDS-PAGE and subject to western blot analysis.

H. Immunoprecipitation and Western Blot Analysis—Cell or tissue lysates were incubated overnight with the appropriate antibodies and Protein G Plus Protein A beads. Beads were washed three times with PBS buffer and then eluted for 30 minutes at RT with SDS-sample buffer. Eluates were separated by SDS-PAGE, electrophoretically transferred to nitrocellulose membranes and blocked in Tris Buffered Saline with 0.1% Tween 20 (TBS-T) containing 5% non-fat dry milk (NFDM) for 1 hr at RT. Membranes were then incubated in 5% NFDM containing primary antibody at 4° C. overnight, washed in TBS-T for 10 minutes three times, incubated in 5% NFDM containing HRP-conjugated secondary antibody, and then washed for 10 min/time three times in TBS-T. Bound antibodies were then revealed using enhanced chemiluminescence reagent (Pierce) and fluorography (HyBlot CL, Denville). Densitometric measurements were made using Quantity One.

I. Statistical Analysis—Data are presented as mean±SEM. Statistical analysis was performed using GraphPad PRISM version 5. Statistical significance was determined by t-test when comparing two groups and by one-way randomized ANOVA followed by Bonferroni's post hoc test when comparing multiple groups or Dunnett's post hoc test when test groups were compared to the control. $p<0.05$ was considered significant.

J. Immunolocalization of ARH Sprague-Dawley rats were fixed by retrograde perfusion and embedded in paraffin. Sections 3 □m thick were picked up on coverslips and heat-induced target retrieval using a citrate buffer, pH 8 was used to unmask epitopes. Sections were then washed and incubated overnight with primary antibodies to ARH raised in goat (Santa Cruz Biotechnology, Santa Cruz, Calif.) at a concentration of 5 ug/ml at 4° C. using methods and marker antibodies described previously. (Coleman R A, et al., *J Histochem Cytochem.* 54(7):817-27, 2006).

What is claimed is:

1. A method of treating hyperkalemia in a human subject in need thereof, comprising administering to the subject a therapeutically effective amount of a protein comprising a biologically active fragment of human autosomal recessive hypercholesterolemia protein, wherein the protein comprises the amino acid sequence of SEQ ID NO:5, or a protein that has at least 90% sequence identity with the amino acid sequence of SEQ ID NO:5, wherein the protein or the biologically active fragment binds human renal outer medullary potassium channel protein without causing endocytosis.

2. The method of claim 1, wherein the biologically active fragment lacks a clathrin box.

3. The method of claim 1, wherein the biologically active fragment either lacks a clathrin box and at least one adaptor AP-2 domain or has a clathrin box but lacks at least one adaptor AP-2 domain.

4. The method of claim 1, wherein the biologically active fragment is a dominant negative autosomal recessive hypercholesterolemia protein comprising the amino acid sequence set forth in SEQ ID NO:7, or a protein that has at least 95% sequence identity with the amino acid sequence of SEQ ID NO:7.

* * * * *